(12) United States Patent
Black et al.

(10) Patent No.: US 11,123,198 B2
(45) Date of Patent: Sep. 21, 2021

(54) EXPANDABLE SPACERS

(71) Applicant: DeGen Medical, Inc., Florence, SC (US)

(72) Inventors: Craig Black, Florence, SC (US); James P. Duncan, Hernando, MS (US)

(73) Assignee: DeGen Medical, Inc., Florence, SC (US)

( * ) Notice: Subject to any disclaimer, the term of this patent is extended or adjusted under 35 U.S.C. 154(b) by 126 days.

(21) Appl. No.: 16/682,196

(22) Filed: Nov. 13, 2019

(65) Prior Publication Data
US 2020/0146840 A1    May 14, 2020

Related U.S. Application Data

(60) Provisional application No. 62/760,503, filed on Nov. 13, 2018.

(51) Int. Cl.
*A61F 2/44* (2006.01)
*A61F 2/46* (2006.01)

(52) U.S. Cl.
CPC .......... *A61F 2/4455* (2013.01); *A61F 2/4611* (2013.01); *A61F 2002/4615* (2013.01)

(58) Field of Classification Search
CPC .. A61F 2/44; A61F 2/4455; A61F 2/46; A61F 2/4611
See application file for complete search history.

(56) References Cited

U.S. PATENT DOCUMENTS

| | | |
|---|---|---|
| 5,653,763 A | 8/1997 | Enrico et al. |
| 5,961,554 A | 10/1999 | Janson et al. |
| 5,980,572 A | 11/1999 | Kim et al. |
| 6,102,950 A | 8/2000 | Vaccaro |
| 6,129,763 A | 10/2000 | Chauvin et al. |
| 6,176,882 B1 | 1/2001 | Biedermann et al. |
| 6,375,682 B1 | 4/2002 | Fleischmann et al. |
| 6,443,989 B1 | 9/2002 | Jackson |
| 6,491,724 B1 | 12/2002 | Ferree |
| 6,558,424 B2 | 5/2003 | Thalgott |
| 6,562,074 B2 | 5/2003 | Gerbec et al. |
| 6,685,742 B1 | 2/2004 | Jackson |
| 6,743,257 B2 | 6/2004 | Castro |

(Continued)

FOREIGN PATENT DOCUMENTS

| | | |
|---|---|---|
| CN | 101460117 | 6/2009 |
| CN | 101049254 | 5/2010 |

(Continued)

OTHER PUBLICATIONS

Aesculap Implant Systems, LLC. "CeSpace XP Interbody System," p. 1, retrieved from Internet Apr. 24, 2014, <URL: http://www.aesculapimplantsystems.com/default.aspx?pageid=3945>.

(Continued)

*Primary Examiner* — Christopher J Beccia
(74) *Attorney, Agent, or Firm* — MacMillan, Sobanski & Todd, LLC

(57) ABSTRACT

The technical description relates to expandable spacer configured to engage an intervertebral disk. An example expandable spacer includes a main body, a first endplate, a second endplate, a driving member, a plurality of pins, and an actuation member. The expandable member is also configured to transition from a first configuration to a second configuration. Additionally, various expandable spacers are described and illustrated herein.

20 Claims, 16 Drawing Sheets

(56) References Cited

U.S. PATENT DOCUMENTS

| | | |
|---|---|---|
| 6,761,739 B2 | 7/2004 | Shepard |
| 7,018,415 B1 | 3/2006 | McKay |
| 7,037,339 B2 | 5/2006 | Houfburg |
| 7,094,257 B2 | 8/2006 | Mujwid et al. |
| 7,137,997 B2 | 11/2006 | Paul |
| 7,220,280 B2 | 5/2007 | Kast et al. |
| 7,396,365 B2 | 7/2008 | Michelson |
| 7,708,779 B2 | 5/2010 | Edie et al. |
| D629,104 S | 12/2010 | Calverley et al. |
| 7,875,078 B2 | 1/2011 | Wysocki et al. |
| 7,875,080 B2 | 1/2011 | Puno et al. |
| 8,025,680 B2 | 9/2011 | Hayes et al. |
| 8,057,548 B2 | 11/2011 | Abemathie et al. |
| 8,062,375 B2 | 11/2011 | Glerum et al. |
| 8,114,092 B2 | 2/2012 | Altarac et al. |
| 8,267,939 B2 | 9/2012 | Cipoletti et al. |
| 8,303,879 B2 | 11/2012 | Bertele et al. |
| 8,328,872 B2 | 12/2012 | Duffield et al. |
| 8,337,530 B2 | 12/2012 | Hestad et al. |
| 8,394,145 B2 | 3/2013 | Weiman |
| 8,425,604 B2 | 4/2013 | Trieu |
| D682,427 S | 5/2013 | Farris et al. |
| 8,496,706 B2 | 7/2013 | Ragab et al. |
| 8,496,713 B2 | 7/2013 | Bennett et al. |
| 8,506,629 B2 | 8/2013 | Weiland |
| 8,518,120 B2 | 8/2013 | Glerum et al. |
| 8,523,910 B2 | 9/2013 | Seifert et al. |
| 8,545,566 B2 | 10/2013 | Niemiec et al. |
| 8,551,176 B2 | 10/2013 | Ulrich, Jr. et al. |
| 8,556,974 B2 | 10/2013 | Suh et al. |
| 8,556,979 B2 | 10/2013 | Glerum et al. |
| 8,597,355 B2 | 12/2013 | Hansell |
| 8,597,359 B2 | 12/2013 | Butler et al. |
| 8,617,244 B2 | 12/2013 | Reichen et al. |
| 8,632,593 B2 | 1/2014 | Suh et al. |
| 8,641,768 B2 | 2/2014 | Duffield et al. |
| 8,679,183 B2 | 3/2014 | Glerum et al. |
| 8,685,064 B2 | 4/2014 | Hestad et al. |
| 8,685,098 B2 | 4/2014 | Glerum et al. |
| 8,696,751 B2 | 4/2014 | Ashley et al. |
| 8,709,086 B2 | 4/2014 | Glerum |
| 8,888,853 B2 | 11/2014 | Glerum et al. |
| 8,888,854 B2 | 11/2014 | Glerum et al. |
| 8,900,309 B2 | 12/2014 | James et al. |
| 8,926,704 B2 | 1/2015 | Glerum et al. |
| 9,039,771 B2 | 5/2015 | Glerum et al. |
| 9,119,730 B2 | 9/2015 | Glerum et al. |
| 9,155,628 B2 | 10/2015 | Glerum et al. |
| 9,204,974 B2 | 12/2015 | Glerum et al. |
| 9,211,196 B2 | 12/2015 | Glerum et al. |
| 9,216,095 B2 | 12/2015 | Glerum et al. |
| 9,216,096 B2 | 12/2015 | Lynn et al. |
| 9,226,836 B2 | 1/2016 | Glerum |
| 9,289,244 B2 | 3/2016 | Hestad et al. |
| 9,358,126 B2 | 6/2016 | Glerum et al. |
| 9,358,128 B2 | 6/2016 | Glerum et al. |
| 9,452,063 B2 | 9/2016 | Glerum et al. |
| 9,456,903 B2 | 10/2016 | Glerum et al. |
| 9,492,287 B2 | 11/2016 | Glerum et al. |
| 9,510,954 B2 | 12/2016 | Glerum et al. |
| 9,532,810 B2 | 1/2017 | Hestad et al. |
| 9,597,200 B2 | 3/2017 | Glerum et al. |
| 9,655,747 B2 | 5/2017 | Glerum et al. |
| 9,757,248 B2 | 9/2017 | Chokshi |
| 9,763,700 B1 | 9/2017 | Gregory |
| 9,848,997 B2 | 12/2017 | Glerum et al. |
| 9,949,841 B2 | 4/2018 | Glerum et al. |
| 9,962,271 B2 | 5/2018 | Glerum |
| 10,034,767 B2 | 7/2018 | Baynham |
| 10,052,213 B2 | 8/2018 | Glerum et al. |
| 10,098,758 B2 | 10/2018 | Matthew et al. |
| 10,154,912 B2 | 12/2018 | Glerum |
| 10,219,913 B2 | 3/2019 | Matthew et al. |
| 10,226,359 B2 | 3/2019 | Glerum et al. |
| 10,299,934 B2 | 5/2019 | Seifert et al. |
| 10,314,721 B2 | 6/2019 | Chokshi |
| 10,327,917 B2 | 6/2019 | Glerum et al. |
| 10,350,081 B2 | 7/2019 | Seifert et al. |
| 10,350,085 B2 | 7/2019 | Glerum et al. |
| 10,463,501 B2 | 11/2019 | Black et al. |
| 2004/0102850 A1 | 5/2004 | Shepard |
| 2005/0149192 A1 | 7/2005 | Zucherman et al. |
| 2007/0032871 A1 | 2/2007 | Michelson |
| 2007/0073400 A1 | 3/2007 | Paul |
| 2007/0293948 A1 | 12/2007 | Bagga et al. |
| 2009/0076616 A1 | 3/2009 | Duggal et al. |
| 2009/0171461 A1 | 7/2009 | Conner et al. |
| 2009/0198278 A1 | 8/2009 | Shibata et al. |
| 2010/0286779 A1 | 11/2010 | Thibodeau |
| 2011/0040384 A1 | 2/2011 | Junn et al. |
| 2011/0160860 A1 | 6/2011 | Johnston et al. |
| 2011/0172769 A1 | 7/2011 | Ganem et al. |
| 2011/0172774 A1 | 7/2011 | Varela |
| 2011/0184522 A1 | 7/2011 | Melkent et al. |
| 2011/0190888 A1 | 8/2011 | Bertele et al. |
| 2011/0224796 A1 | 9/2011 | Weiland et al. |
| 2011/0307016 A1 | 12/2011 | Reglos et al. |
| 2012/0078370 A1 | 3/2012 | James et al. |
| 2012/0089191 A1 | 4/2012 | Altarac et al. |
| 2012/0136443 A1 | 5/2012 | Wenzel |
| 2012/0316649 A1 | 12/2012 | Johnston et al. |
| 2013/0030544 A1 | 1/2013 | Studer |
| 2013/0060339 A1 | 3/2013 | Duffield et al. |
| 2013/0131726 A1 | 5/2013 | Suh et al. |
| 2013/0144388 A1 | 6/2013 | Emery et al. |
| 2013/0158667 A1 | 6/2013 | Tabor et al. |
| 2013/0158669 A1 | 6/2013 | Sungarian et al. |
| 2014/0012382 A1 | 1/2014 | Doty |
| 2014/0163682 A1 | 6/2014 | Iott et al. |
| 2014/0236297 A1 | 8/2014 | Iott et al. |
| 2014/0277474 A1 | 9/2014 | Robinson et al. |
| 2015/0100128 A1 | 4/2015 | Glerum et al. |
| 2015/0100129 A1 | 4/2015 | Waugh et al. |
| 2015/0272743 A1 | 10/2015 | Jimenez et al. |
| 2015/0342748 A1 | 12/2015 | Baynham |
| 2015/0342749 A1 | 12/2015 | Baynham |
| 2017/0035577 A1 | 2/2017 | Iott et al. |
| 2017/0156885 A1 | 6/2017 | Zur et al. |
| 2017/0281432 A1 | 10/2017 | Glerum et al. |
| 2018/0161071 A1 | 6/2018 | Gregory |
| 2018/0207002 A1 | 7/2018 | Glerum et al. |
| 2018/0289508 A1 | 10/2018 | Glerum |
| 2018/0338840 A1 | 11/2018 | Glerum et al. |
| 2019/0021871 A1 | 1/2019 | Baynham |
| 2019/0282374 A1 | 9/2019 | Chokshi |

FOREIGN PATENT DOCUMENTS

| | | |
|---|---|---|
| EP | 2025307 | 2/2009 |
| EP | 2942036 | 11/2015 |
| WO | WO2011047230 | 4/2011 |
| WO | WO2013152257 | 10/2013 |
| WO | WO2013158960 | 10/2013 |
| WO | WO2014028635 | 2/2014 |
| WO | WO2014071268 | 5/2014 |
| WO | WO2014093430 | 6/2014 |
| WO | WO2014151165 | 9/2014 |
| WO | WO2014165319 | 10/2014 |
| WO | WO2015198335 | 12/2015 |
| WO | WO2017189416 | 11/2017 |

OTHER PUBLICATIONS

Synthes Spine, "Advanced ACF Spacer: An allograft spacer with demineralized surfaces for anterior cervical interbody fusion," Synthes. com, 2004, pp. 1-7.

Lemcke, Johannes, et al., "Polyetheretherketone (PEEK) Spacers for Anterior Cervical Fusion: A Retrospective Comparative Effectiveness Clinical Trial," Open Orthop. J. 2011; 5: 348-353.

Bonovo Orthopedics, "NuVasive PCM Cervical Disc," pp. 1-9, accessed Feb. 26, 2014, http://www.bonovo-ortho.com/Products/Spine(Cervical).php.

(56) References Cited

OTHER PUBLICATIONS

Depuy Spine, "Surgical Technique: VG2 Cervical Allograft," Brochure from Depuy Spine, Virginia Beach, VA, 2003.

Globus Medical, "Sustain & Sustain-R, Large, Trapezoidal thoracolumbar vertebral body replacement device," pp. 1-3, retrieved from Internet Feb. 26, 2014, <URL:http://www.globusmedical.com/portfolio/sustain-sustain-r-large/>.

Globus Medical, "Colonial, cervical interbody fusion device," pp. 1-2, retrieved from Internet Feb. 26, 2014, <URL: http://globusmedical.com/portfolio/colonial/>.

*Globus Medical Inc. V. Depuy Synthes Products, LLC, Depuy Synthes Sales, Inc.*, Complaint, Case No. 1:13-cv-00854-UNA, at pp. 1-5 (D. Del. May 15, 2013).

Ho, Cheng, et al., "Kurokawa-type Laminoplasty using Hydroxyapatite Spacer for Cervical Myelopathy," Hong Kong J. Orthop. Surg. 2004:8 (1):12-21.

Mahe Medical, "Perfect Spine, Vertebral Spacer System," from www.slideshare.net, slide No. 10, accessed Feb. 26, 2014, http://image.slidesharecdn.com/cages-130721071738-phpapp02/95/slide-10-638.jpg?cb=1374409152.

Niu, Chi-Chien et al., "Trapezoidal Titanium Cage in Anterior Cervical Interbody Fusion: A Clinical Experience," Chang Gung Med. J. Apr. 2005; 28 (4): 212-221.

Nutech Medical, "Interbody," Nutchmedical.com, pp. 1-3, accessed Feb. 26, 2014, http://nutechmedical.com/products/spine/interbody/.

Gelisim Medical, "Spinal Cerrahi", Gelisimmedikal.com, pp. 1-2, 2013, accessed Jun. 27, 2014, http://www.gelisimmedikal.com/eng/servical-peek-cage.asp.

Lexis Totalpatentone. English Translation of Abstract of CN 101049254, retrieved from Internet on Jun. 6, 2017, p. 1.

Atlas Spine. "HiJAK AC," p. 1, retrieved from Internet Mar. 5, 2019, <URL: https://www.atlasspine.com/hijak-ac>.

Frisch et al. "Static versus Expandable Interbody Spacers: Preliminary 1-Year Clinical and Radiographic Results," Journal of Clinical Neurology, Neurosurgery and Spine, published Dec. 1, 2017, pp. 1-9, 1(1):113.

Exactech Spine. "Octane M Modular PEEK Spacer System," retrieved from Internet, pp. 1-16.

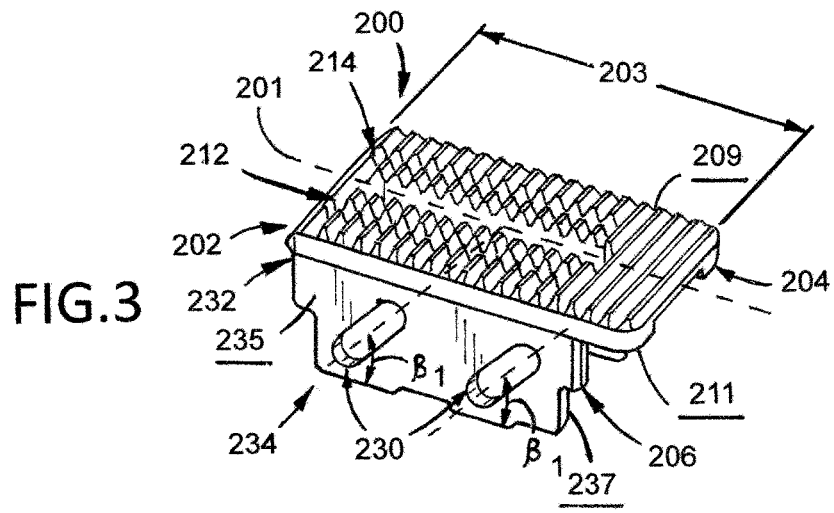
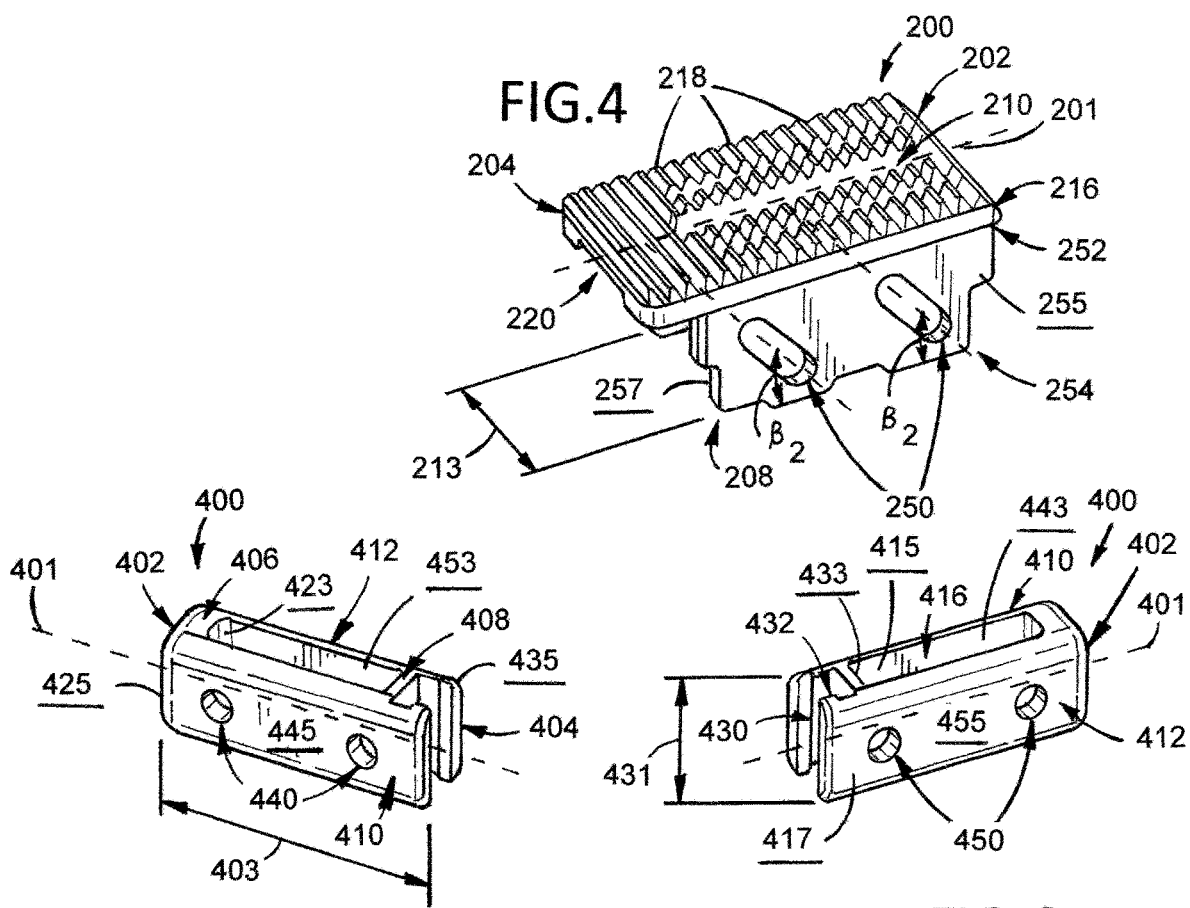

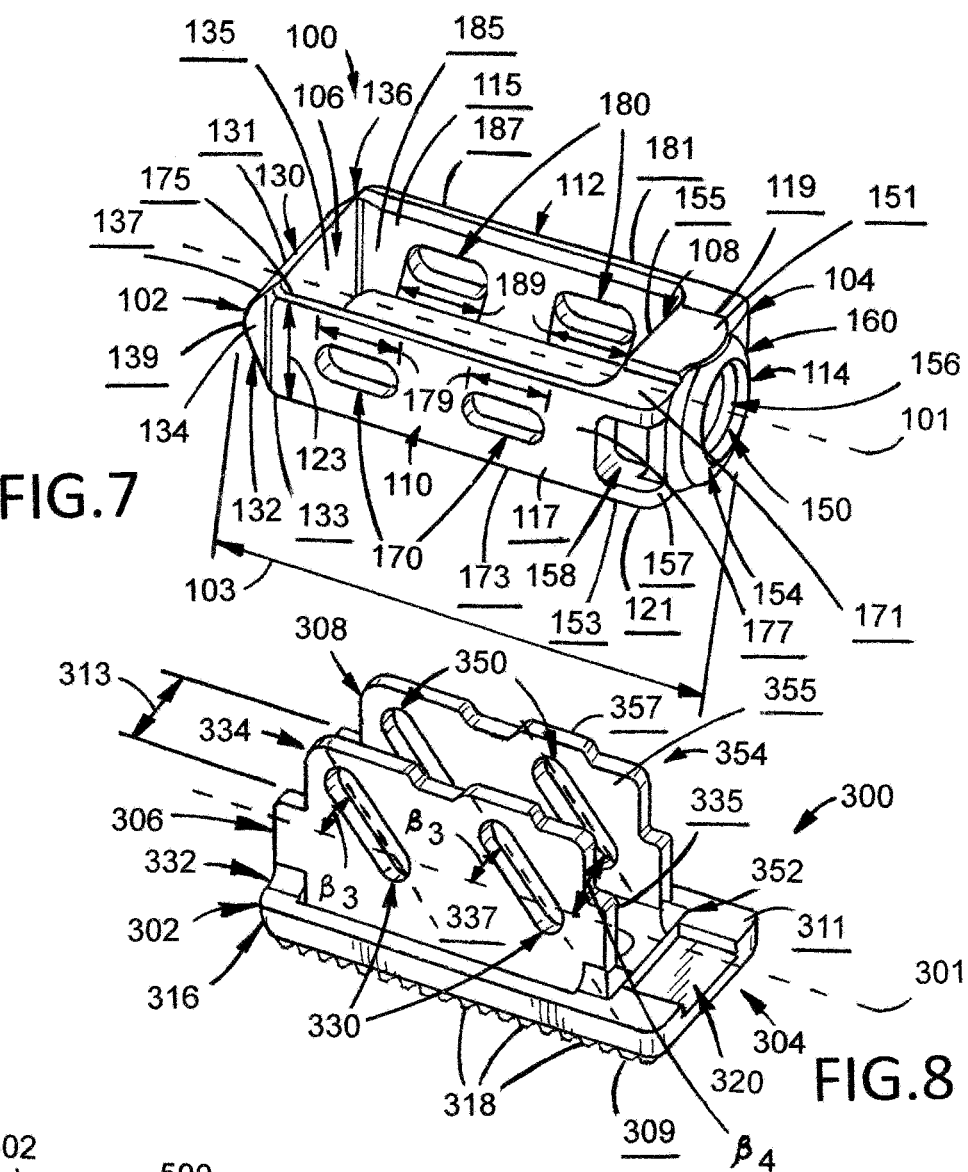
FIG. 7
FIG. 8
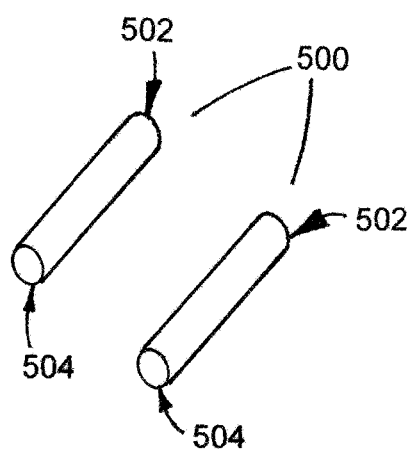
FIG. 9
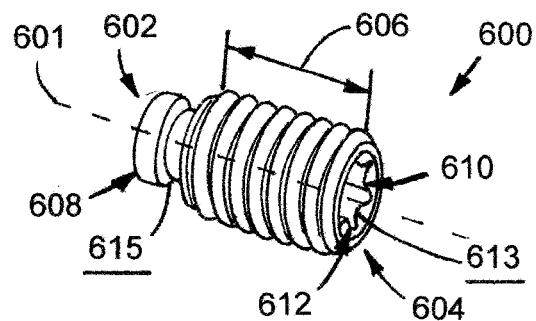
FIG. 10

EXPANDABLE SPACERS

FIELD

The disclosure relates to the field of implantable medical devices. More particularly, the disclosure relates to medical devices suitable for implantation in spaces between bones, such as spaces between vertebral bodies in a spinal column of a vertebrate. Specific examples relate to expandable spacers suitable for implantation between adjacent vertebral bodies of a spinal column.

BACKGROUND

Bone degeneration can be caused by trauma, disease, and natural processes, such as aging, which can have a negative impact on the lifestyle of an animal. For example, destabilization of a spine in a vertebrate, such as human being, may result in alteration of the spacing between the adjacent vertebral bodies. This destabilization can place pressure onto the surrounding nerves and tissues between the vertebral bodies causing pain, discomfort, and, eventually, nerve damage.

To alleviate the pain and discomfort caused by the destabilization of the spacing between the adjacent vertebral bodies is to implant a medical device into the space between two adjacent vertebral bodies. This implantation of the medical device supports the structure of the spine by maintaining a desired spacing and proper angular positioning of the spinal column.

Various expandable spacers for use during interspinous spacer implantation are known in the art. Known expandable spacers, however, have several drawbacks. For example, expandable spacers used in interspinous spacer implantation surgeries do not allow users, such as surgeons, to easily place and expand the expandable spacers due to these expandable spacers comprising larger heights in a first configuration. Furthermore, the expandable spacers known in art do not allow users to easily assemble or disassemble while in use.

A need exists, therefore, for improved expandable spacers.

BRIEF SUMMARY OF SELECTED EXAMPLES

An example expandable spacer includes a main body, a first endplate, a second endplate, a driving member, a plurality of pins, and an actuation member. The expandable spacer has a first configuration and a second configuration and is configured to engage a vertebral body. The main body has a main body first lateral wall, a main body second lateral wall that has a threaded opening, a main body inner surface, and a main body outer surface. The main body also has a main body third lateral wall that connects the main body first lateral wall to the main body second lateral wall and includes at least one opening that extends entirely through the main body third lateral wall. The main body also has a main body fourth lateral wall that connects the main body first lateral wall to the main body second lateral wall and includes at least one opening that extends entirely through the main body fourth lateral wall. The main body first lateral wall, the main body second lateral wall, the main body third lateral wall, and the main body fourth lateral wall cooperatively define a main body interior chamber. The first endplate includes a first endplate first end, a first endplate second end, a first endplate inner surface, and a first endplate outer surface. Additionally, the first endplate has at least one first endplate slot that extends between the first endplate inner surface and the first endplate outer surface and at least one first endplate extension that extends from the first endplate inner surface towards the main body and includes at least one opening. The second endplate includes a second endplate first end, a second endplate second end, a second endplate inner surface, and a second endplate outer surface. Additionally, the second endplate has at least one second endplate slot that extends between the second endplate inner surface to the second endplate outer surface and at least one second endplate extension that extends from the second endplate inner surface towards the main body and including at least one opening. The driving member is disposed within the main body interior cavity and has a driving member first lateral wall, a driving member second lateral wall, a driving member third lateral wall, and a driving member fourth lateral wall. The driving member second lateral wall has a channel that is disposed on a plane parallel to the driving member second lateral wall. The driving member third lateral wall has at least one opening that extends entirely through the driving member third lateral wall, the driving member fourth lateral wall has at least one opening that extends entirely through the driving member fourth lateral wall. The actuation member is configured to be inserted into the threaded opening and defines a cam to interface with the channel of the driving member to transition the expandable spacer from the first configuration to the second configuration. Each pin of the plurality of pins has a first end and a second end. Additionally, the first end or the second end of each pin is passed through and received by one opening disposed on the main body, one opening disposed on the first endplate, one opening disposed on the second endplate, and one opening disposed on the driving member to assemble the main body, the first endplate, the second endplate, and the driving member together.

Another example expandable spacer includes a main body, a first endplate, a second endplate, a driving member, a plurality of pins, and an actuation member. The expandable spacer having a first configuration and a second configuration and configured to engage a vertebral body. The main body has a main body first lateral wall, a main body second lateral wall that has a threaded opening, a main body inner surface, a main body outer surface. The main body also has a main body third lateral wall that connects the main body first lateral wall to the main body second lateral wall and includes at least one opening that extends entirely through the main body third lateral wall. The main body also includes a main body fourth lateral wall that connects the main body first lateral wall to the main body second lateral wall and includes at least one opening that extends entirely through the main body fourth lateral wall. The main body first lateral wall, the main body second lateral wall, the main body third lateral wall, and the main body fourth lateral wall cooperatively define a main body interior chamber. The first endplate has a first endplate first end, a first endplate second end, a first endplate inner surface, and a first endplate outer surface. The first endplate also has at least two first endplate slots that extend between the first endplate inner surface and the first endplate outer surface. The first extension extends from the first endplate inner surface towards the main body and includes at least two openings. The second extension extends from the first endplate inner surface towards the main body and includes at least two openings. The second endplate has a second endplate first end, a second endplate second end, a second endplate inner surface, and a second endplate outer surface. The second endplate has at least one second endplate slot that extends between the second endplate inner surface to the second endplate outer surface. The third extension extends from the second endplate inner surface towards the main body and includes at least one opening. The fourth extension extends from the second endplate inner surface towards the main body and includes at least two openings. The driving member is disposed within the main body interior cavity and has a driving member first lateral wall, a driving member second lateral wall, a driving member third lateral wall, and a driving member fourth lateral wall. The driving member second lateral wall has a channel that is disposed on a plane parallel to the driving member second lateral wall. The driving member third lateral wall has at one opening that extends entirely through the driving member third lateral wall. The driving member fourth lateral wall has at least one opening that extends entirely through the driving member fourth lateral wall. The actuation member is configured to be inserted into the threaded opening and defines a cam to interface with the channel of the driving member to transition the expandable spacer from the first configuration to the second configuration. Each pin of the plurality of pins has a first end and a second end. The first end or the second end of each pin is passed through and received by one opening disposed on the main body, one opening disposed on the first endplate, one opening disposed on the second endplate, and one opening disposed on the driving member to assemble the main body, the first endplate, the second endplate, and the driving member together.

Another example expandable spacer includes a main body, a first endplate, a second endplate, a driving member, a plurality of pins, and an actuation member. The expandable spacer having a first configuration and a second configuration and configured to engage a vertebral body. The main body has a main body first lateral wall, a main body second lateral wall that has a threaded opening, a main body inner surface, and a main body outer surface. The main body has a main body third lateral wall that connects the main body first lateral wall to the main body second lateral wall and includes two openings that are equally spaced along the main body third lateral wall that extend entirely through the main body third lateral wall. The main body fourth lateral wall connects the main body first lateral wall to the main body second lateral wall and includes two openings that are equally spaced along the main body third lateral wall that extend entirely through the main body fourth lateral wall. The main body first lateral wall, the main body second lateral wall, the main body third lateral wall, and the main body fourth lateral wall cooperatively define a main body interior chamber. The first endplate has a first endplate first end, a first endplate second end, a first endplate inner surface, and a first endplate outer surface. The first endplate also has a first, second, and third oblong first endplate slots that extend between the first endplate inner surface and the first endplate outer surface. The first extension extends from the first endplate inner surface towards the main body and includes at least two oblong openings. The second extension extends from the first endplate inner surface towards the main body and includes at least two oblong openings. The second endplate has a second endplate first end, a second endplate second end, a second endplate inner surface, and a second endplate outer surface. The second endplate also has first, second, and third oblong second endplate slot that extend between the second endplate inner surface to the second endplate outer surface. The third extension extends from the second endplate inner surface towards the main body and includes at least one opening. The fourth extension extends from the second endplate inner surface towards the main body and includes at least two oblong openings. The driving member is disposed within the main body interior cavity and comprises a driving member first lateral wall, a driving member second lateral wall, a driving member third lateral wall, and a driving member fourth lateral wall. The driving member second lateral wall has a channel that is disposed on a plane parallel to the driving member second lateral wall. The driving member third lateral wall has two openings that are equally spaced along the driving member third lateral wall and extend entirely through the driving member third lateral wall. The driving member fourth lateral wall has two openings that are equally spaced along the main body third lateral wall and extend entirely through the driving member fourth lateral wall. The actuation member is configured to be inserted into the threaded opening and defines a cam to interface with the channel of the driving member to transition the expandable spacer from the first configuration to the second configuration. Each pin of the plurality of pins has a first end and a second end. The first end or the second end of each pin is passed through and received by one opening disposed on the main body, one opening disposed on the first endplate, one opening disposed on the second endplate, and one opening disposed on the driving member to assemble the main body, the first endplate, the second endplate, and the driving member together.

DESCRIPTION OF FIGURES

FIG. 3 is a perspective view of the first endplate of the example expandable spacer illustrated in FIG. 1.

FIG. 4 is a perspective view of the first endplate of the example expandable spacer illustrated in FIG. 1.

FIG. 5 is a perspective view of the driving member of the example expandable spacer illustrated in FIG. 2.

FIG. 6 is a perspective view of the driving member of the example expandable spacer illustrated in FIG. 2.

FIG. 7 is a perspective view of the main body of the example expandable spacer illustrated in FIG. 1.

FIG. 8 is a perspective view of the second endplate of the example expandable spacer illustrated in FIG. 1.

FIG. 9 is a perspective view of the plurality of pins of the example expandable spacer illustrated in FIG. 1.

FIG. 10 is a perspective view of the actuation member of the example expandable spacer illustrated in FIG. 1.

DESCRIPTION OF SELECTED EXAMPLES

The following detailed description and the appended drawings describe and illustrate various example expandable spacers. The description and drawings are provided to enable one skilled in the art to make and use one or more example expandable spacers. They are not intended to limit the scope of the claims in any manner.

Figure 1:
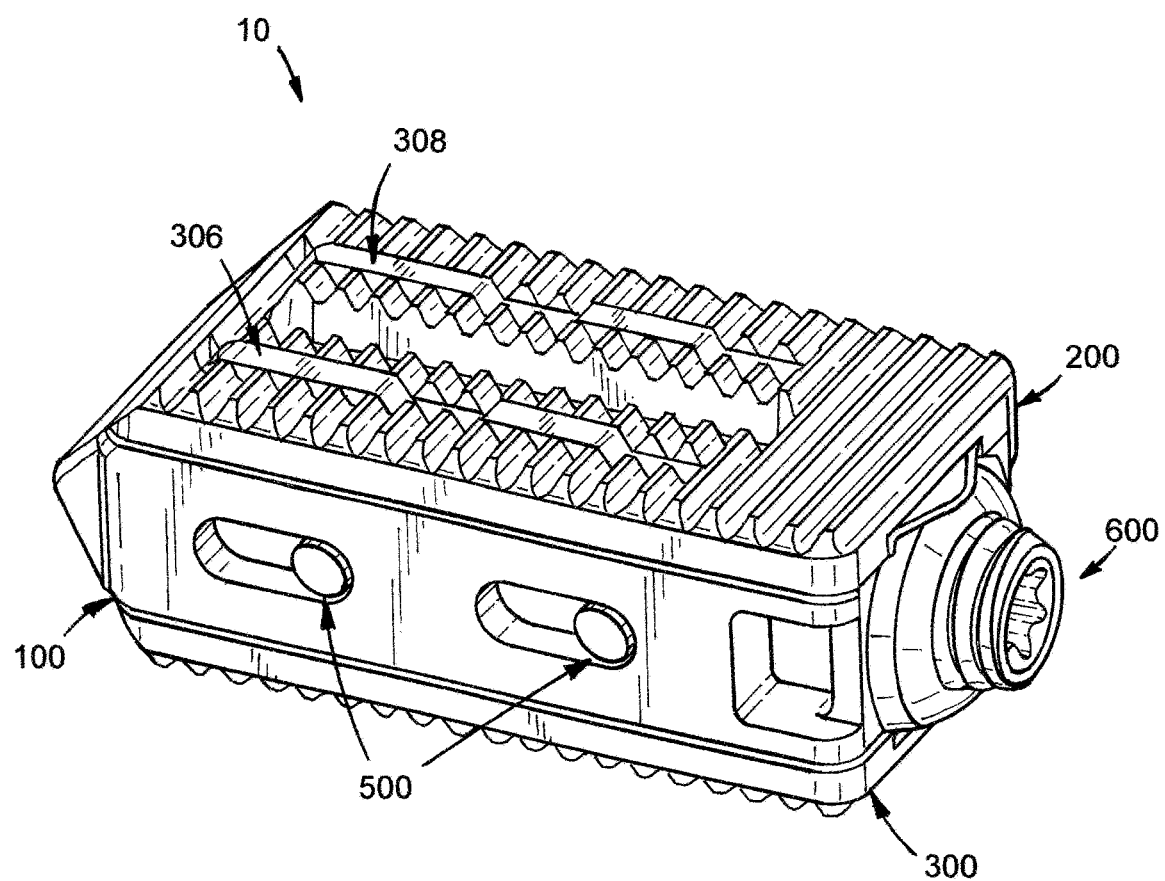
FIG. 1 is a perspective view of an example expandable spacer.
Figure 2:
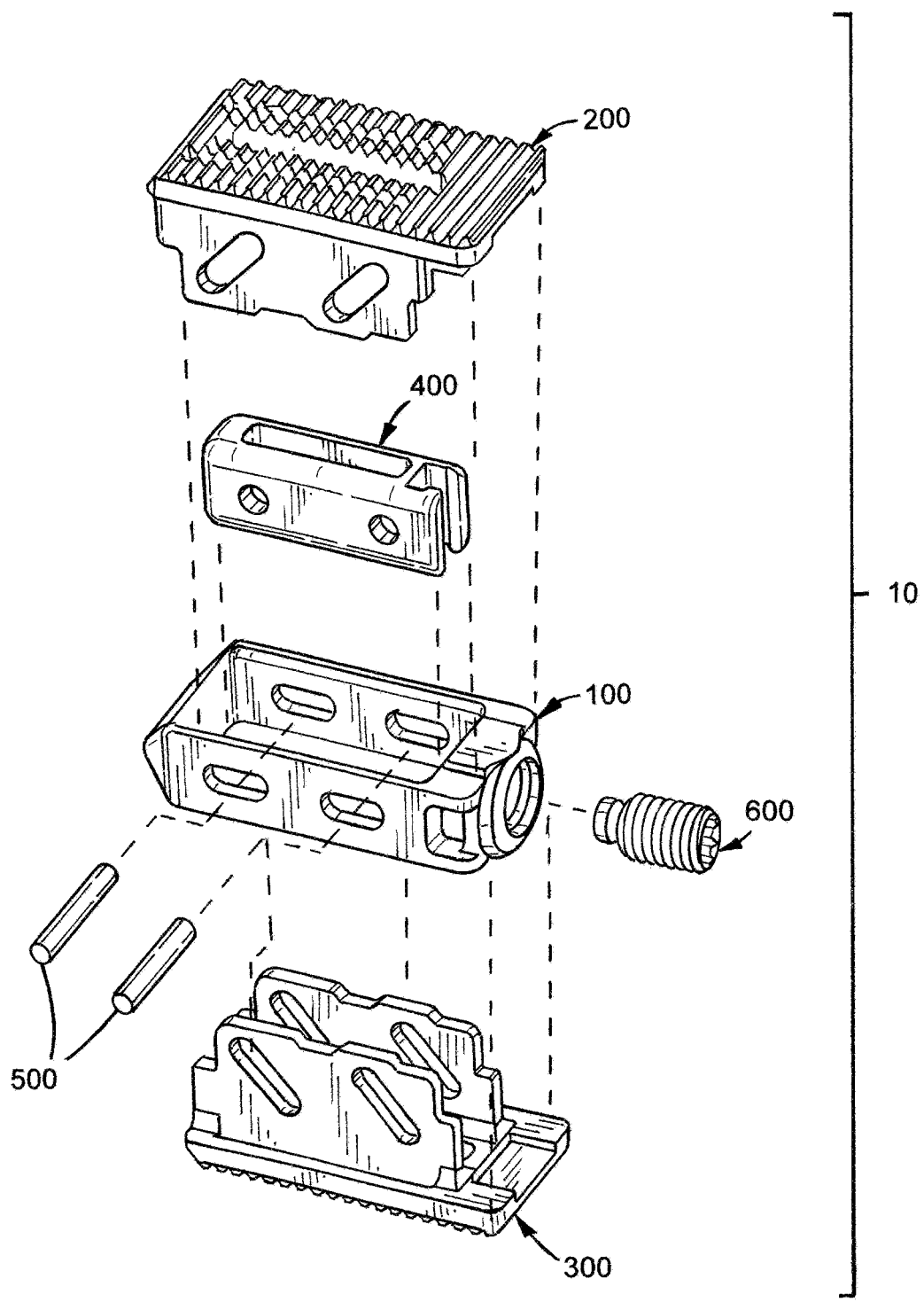
FIG. 2 is an exploded view of the example expandable spacer illustrated in FIG. 1.
Figure 12:
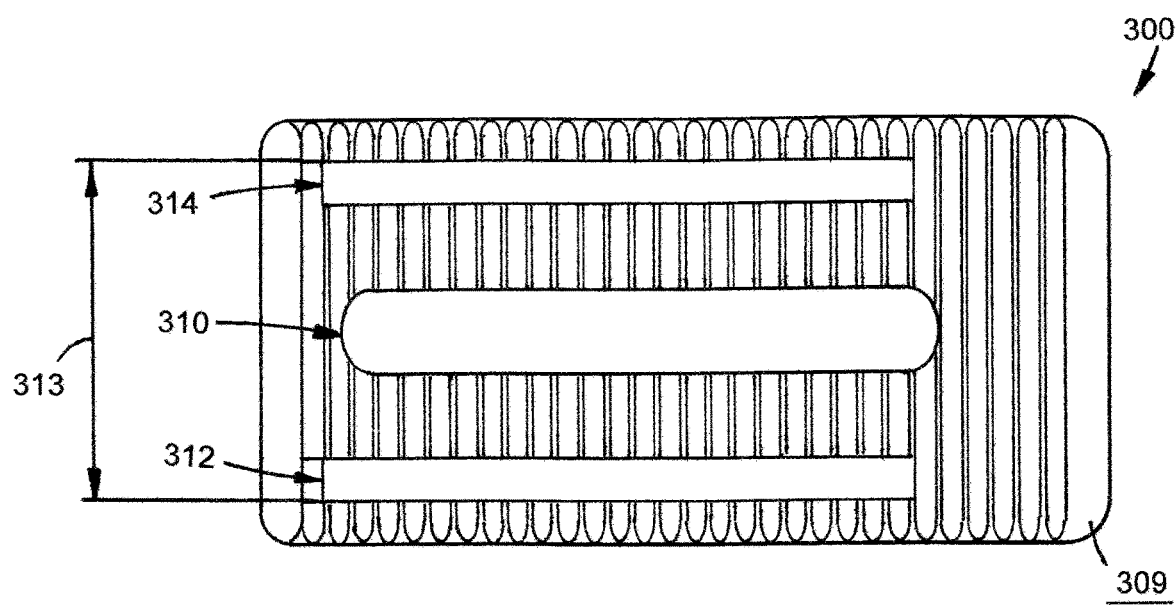
FIG. 12 is a top view of the second endplate of the example expandable spacer illustrated in FIG. 1.
Figure 13:
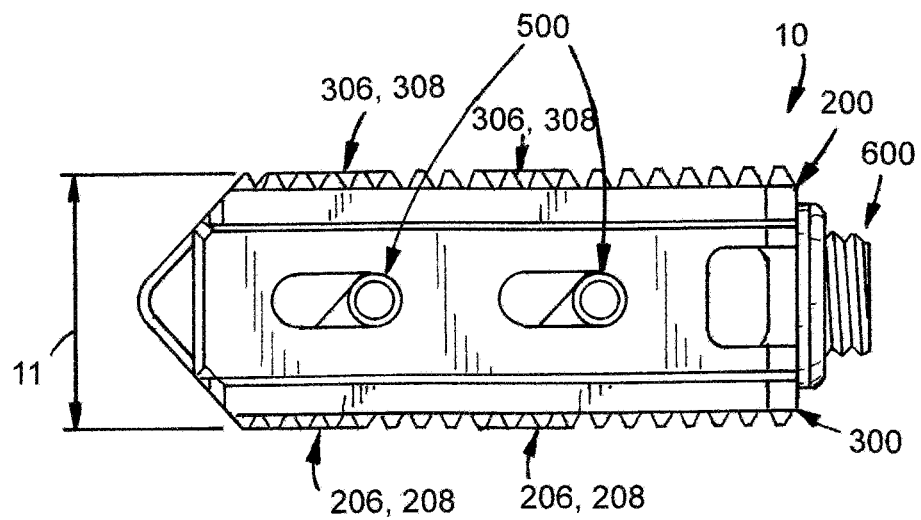
FIG. 13 is a side view of the example expandable spacer illustrated in FIG. 1. The expandable spacer is shown in the first configuration.
Figure 14:
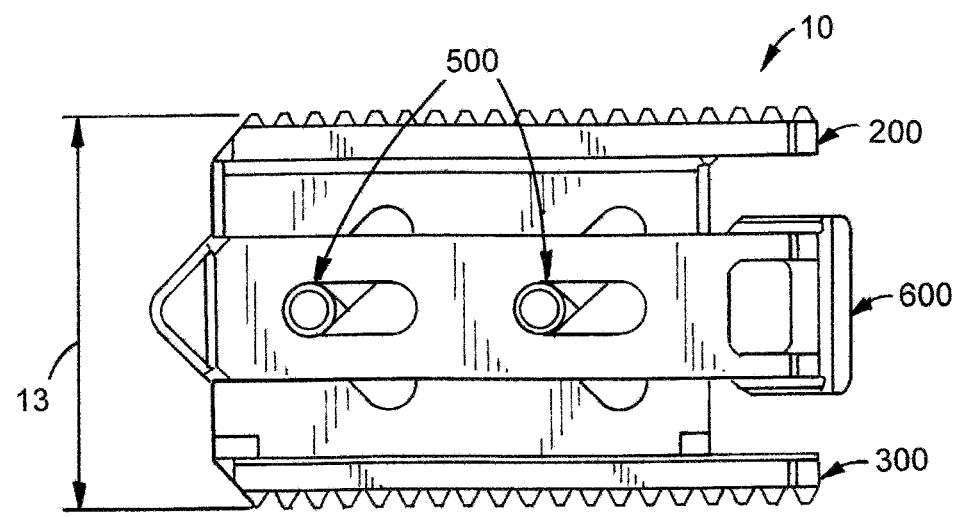
FIG. 14 is a side view of the example expandable spacer illustrated in FIG. 1. The expandable spacer is shown in the second configuration.
Figure 15:
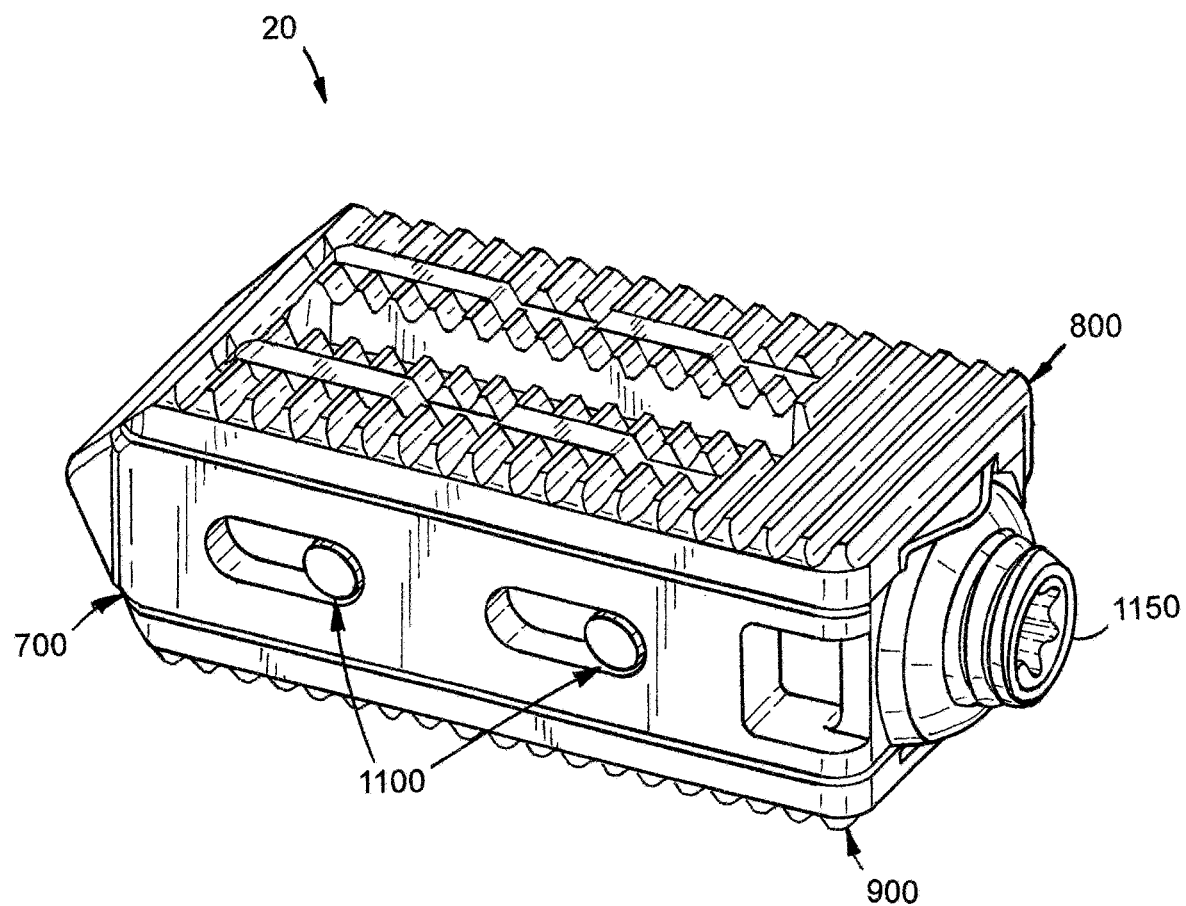
FIG. 15 is a perspective view of another example expandable spacer.
Figure 16:
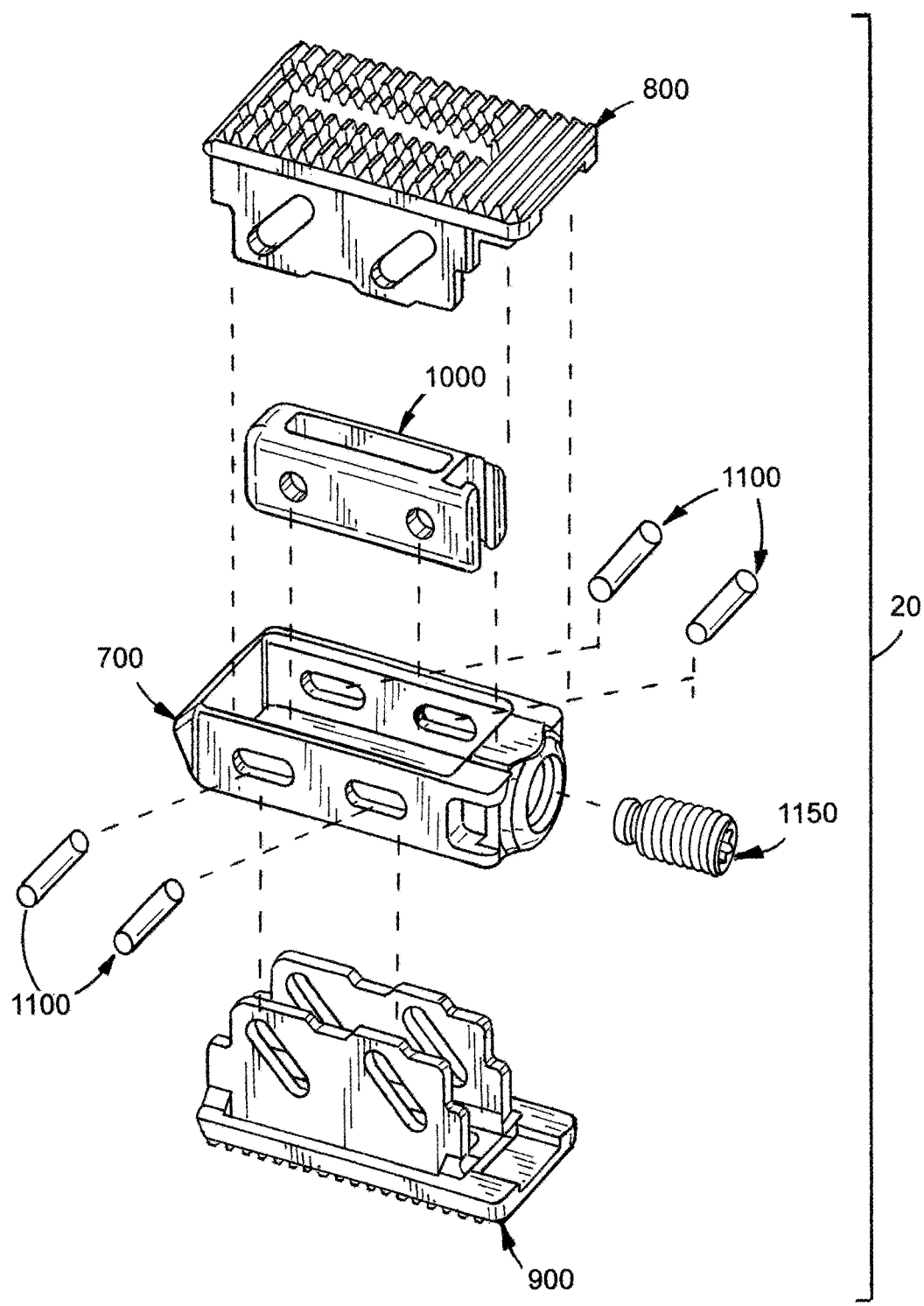
FIG. 16 is an exploded view of the example expandable spacer illustrated in FIG. 15.

Each of the FIGS. 1, 2, 3, 4, 5, 6, 7, 8, 9, 10, 11, 12, 13, and 14 illustrates an example expandable spacer 10 or one or more components thereof. The expandable spacer 10 comprises a main body 100, a first endplate 200, a second endplate 300, a driving member 400, a plurality of pins 500, and an actuation member 600. The expandable spacer 10 is movable between a first configuration and a second configuration. In the first configuration, as illustrated in FIGS. 1 and 13, each of the first endplate 200 and second endplate 300 interfaces with the main body 100. Also, each of the driving member 400, each pin of the plurality of pins 500, and the actuation member 600 is in a first position. In the second configuration, as illustrated in FIG. 14, each of the first and second endplates 200, 300 is spaced such that the distance between the first and second endplates 200, 300 has increased as compared to the first configuration. The expandable spacer 10 moves between the first configuration and the second configuration through rotational movement of the actuation member 600, which forces the driving member 400 to move linearly along a longitudinal axis of the expandable spacer 10. This linear movement of the driving member 400 also moves each pin of the plurality of pins 500, which, as a result of their disposition in respective openings 230, 250, 330, 350 in the respective endplates 200, 300, forces the first and second endplates 200, 300 away from each other in opposing direction along an axis transverse to the longitudinal axis.

The main body 100 has a main body first end 102, a main body second end 104, a lengthwise axis 101 extending between the main body first end 102 to the main body second end 104, a main body first lateral wall 106, a main body second lateral wall 108, a main body third lateral wall 110, a main body fourth lateral wall 112, and a threaded opening 114, a main body inner surface 115, a main body outer surface 117, a main body top surface 119, and a main body bottom surface 121. The main body first lateral wall 106 has an upper surface 131, an opposing lower surface 133, an inner surface 135, and an opposing outer surface 137. The main body second lateral wall 108 has an upper surface 151, an opposing lower surface 153, an inner surface 155, and an opposing outer surface 157. The main body third lateral wall 110 has an upper surface 171, an opposing lower surface 173, an inner surface 175, and an opposing outer surface 177. The main body fourth lateral wall 112 has an upper surface 181, an opposing lower surface 183, an inner surface 185, and an opposing outer surface 187. The inner surfaces 135, 155, 175, 185 of the main body first lateral wall 106, main body second lateral wall 108, main body third lateral wall 110, and main body fourth lateral wall 112 cooperatively define a main body interior chamber 116. Similarly, the opposing outer surfaces 137, 157, 177, 187 of the main body first lateral wall 106, main body second lateral wall 108, main body third lateral wall 110, and main body fourth lateral wall 112 cooperatively define a main body outer surface 117. The upper surfaces 131, 151, 171, 181 of the main body first lateral wall 106, main body second lateral wall 108, main body third lateral wall 110, and main body fourth lateral wall 112 cooperatively define a main body upper surface 119. Similarly, the opposing lower surfaces 133, 153, 175, 185 of the main body first lateral wall 106, main body second lateral wall 108, main body third lateral wall 110, and main body fourth lateral wall 112 cooperatively define a main body lower surface 121. Additionally, the main body 100 is defined by a length 103 that is measured from the main body first end 102 to the main body second end 104.

As illustrated in FIG. 7, the main body first end 102 defines the main body first lateral wall 106, a first depressed portion 130, a second depressed portion 132, a third depressed portion 134, and a fourth depressed portion 136. Each of the first, second, third, and fourth depressed portions 130, 132, 134, 136 extends from the main body first lateral wall 106 to the main body first end 102 to define a sufficiently rounded curvilinear edge 139. The first depressed portion 130 is measured at a first angle (not illustrated) relative to the lengthwise axis 101 of the main body 100, and the second depressed portion 132 is measured at a second angle (not illustrated) relative to lengthwise axis 101 of the main body 100. In the illustrated embodiment, the first and second angles of the first and second depressed portions 130, 132 are congruent angles. The first and second depressed portions 130, 132 may define any suitable first and second angles. A skilled artisan will be able to determine suitable first and second angles for the first and second depressed portions 130, 132 according to a particular example based on various considerations, including the actual and/or expected dimensions of the space between the vertebral bodies and/or the actual and/or expected dimensions of the intervertebral space. An example of suitable first and second angles includes an angle about 45°. The third depressed portion 134 is measured at a third angle (not illustrated) relative to the lengthwise axis 101 of the main body 100 and the fourth depressed portion 136 is measured at a fourth angle (not illustrated) relative to the lengthwise axis 101 of the main body 100. The third and fourth angles of the third and fourth depressed portions 134, 136 are congruent angles. The third and fourth depressed portions 134, 136 may define any suitable third and fourth angles. A skilled artisan will be able to determine suitable third and fourth angles for the third and fourth depressed portions 134, 136 according to a particular example based on various considerations, including the actual and/or expected dimensions of the space between the vertebral bodies and/or the actual and/or expected dimensions of the intervertebral space. An example of suitable third and fourth angles includes an angle about 60°.

As illustrated in FIG. 7, the main body second end 104 defines the main body second lateral wall 108, a threaded opening 150, a first recess 156, and a second recess 158. The main body second lateral wall 108 defines a main body second lateral wall opening (not illustrated) in the medial portion of the main body second lateral wall 108. As best illustrated in FIG. 7, the threaded opening 150 has a threaded opening first end (not illustrated), a threaded opening second end 154, and a groove 156. The threaded opening first end is disposed towards the main body second lateral wall 108, and the threaded opening second end 154 is disposed at the main body second end 104. The groove 156 extends from the threaded opening second end 154, through the threaded opening 150, and terminates at the opening 156 of the second lateral wall 108. The groove 156 is sized and configured to mate with a threading 606 of the actuation member 600, which is described in detail below.

Furthermore, the first and second recesses 158, 160 are disposed toward the main body second end 104. As illustrated in Figures FIG. 7, the first recess 158 is disposed on the main body third lateral wall 110 and the second recess 160 is disposed on the main body fourth lateral wall 112. The first recess 158 is defined between the main body top surface 119 and the main body bottom surface 121 and between the main body second end 104 towards the main body interior chamber 116. The second recess 160 is defined between the main body top surface 119 and the main body bottom surface 121 and between the main body second end 104 toward the main body interior chamber 116. In the illustrated embodiment, first and second recesses 156, 158 are equal in size, shape, and configuration. In addition, each of the first and second recesses 158, 160 are considered advantageous at least because the first and second recesses 158, 160 are sized and configured to receive an insertion instrument (not illustrated in the embodiment) to assist in inserting the expandable spacer 10 into an intervertebral space.

As illustrated in FIG. 7, the main body third lateral wall 110 has a main body first set of openings 170, and the main body fourth lateral wall 112 has a main body second set of openings 180. Each opening of the main body first set of openings 170 extends entirely through the main body third lateral wall 110 such that each opening extends from the main body inner surface 115 to the main body outer surface 117. Similarly, each opening of the main body second set of openings 180 extends entirely through the main body fourth lateral wall 112 such that each opening extends between the main body inner surface 115 to the main body outer surface 117. In the illustrated embodiment, each opening of the main body first set of openings 170 on the main body third lateral wall 110 is directly aligned with each opening of the main body second set of openings 180 on the main body fourth lateral wall 112 such that the main body first set of openings 170 and the main body second set of openings 180 directly oppose each other. Each opening of the main body first set of openings 170 and the main body second set of openings 180 is sized and configured to receive a pin from a plurality of pins 500, which is described in detail below. The alignment and the configuration of each opening of the main body first and second set of openings 170, 180 is considered advantageous at least because a pin from the plurality of pins 500 is able to pass through either the first or second set of openings 170, 180 to connect and link the main body 100, the first endplate 200, the second endplate 300, and the driving member 400 together in order for the expandable spacer 10 to transition from a first configuration to a second configuration. Furthermore, each opening of the main body first set of openings 170 has a length 179, and each opening of the main body second set of openings has a length 189. The lengths 179,189 for the main body first and second sets of openings 170, 180 are measured between the main body first end 102 and the medial portion of the main body 100 or between the main body second end 104 and the medial portion of the main body 100.

Each opening of the main body first and second set of openings 170, 180 can have any suitable size, shape, and configuration, and a skilled artisan will be able to select suitable size, shape, and configuration parameters for an opening in a main body set of openings of an expandable spacer according to a particular embodiment based on various considerations, including the size of a pin passing through the openings, the overall height difference between the first configuration to the second configuration, and other considerations. Additionally, each opening of the main body first and second set of openings 170, 180 can have any suitable structural configuration. Examples of suitable structural configurations include, but are not limited to, elongated circular shapes, elongated rectangular shapes, ovoid, elliptical, and any other suitable structural configuration. In the illustrated embodiment, each opening of the main body first and second set of openings 170, 180 illustrates an oblong rectangular shape.

As illustrated in FIGS. 3 and 4, the first endplate 200 has a first endplate first end 202, a first endplate second end 204, a lengthwise axis 201 extending between the first endplate first end 202 to the first endplate second end 204, a first extension 206, a second extension 208, a first endplate top surface 209, and a first endplate bottom surface 211. The first endplate 200 is also defined by a length 203 that is measured from the first endplate first end 202 to the first endplate second end 204.

The first endplate top surface 209 and the first endplate bottom surface 211 lie on the same plane but directly oppose each other. As illustrated in FIGS. 3 and 4, the first endplate top surface 209 defines a first endplate depressed portion 216 that extends from the medial portion of the first endplate 200 towards the first endplate first end 202. When the expandable spacer 10 is in its first configuration, the first endplate depressed portion 216 is continuous with the first depressed portion 130 of the main body 100 such that the first endplate depressed portion 216 lies on the same plane as the main body first depressed portion 130. The first endplate top surface 209 also defines a set of protruding ridges 218 that extend between the first endplate depressed portion 216 to the first endplate second end 204. Furthermore, as illustrated in FIGS. 3 and 4, the first endplate bottom surface 211 defines the first and second extensions 206, 208 and a first endplate bottom surface notch 220. The first endplate bottom surface notch 220 is disposed on the first endplate second end 204 and extends towards the medial portion of the first endplate 200, and the first endplate bottom surface notch 220 is sized and configured to receive and interface with the threaded opening 114 of the main body 100 when the expandable spacer 10 is in its first configuration.

The first extension 206 has a first extension first end 232 and a first extension second end 234, and the second extension 208 has a second extension first end 252 and a second extension second end 254. In the illustrated embodiment, the first and second extensions 206, 208 of the first endplate 200 are disposed on the first endplate bottom surface 211 and extend away from the first endplate bottom surface 211. As illustrated in FIGS. 3 and 4, the first and second extensions 206, 208 lie on the same plane and are parallel to each other, but directly oppose each other. The first extension 206 includes a first set of openings 230 that are positioned at a first angle $\beta_1$ relative to the lengthwise axis 201 of the first endplate 200. Similarly, the second extension 208 includes a second set of openings 250 that are positioned at a second angle $\beta_2$ relative to the lengthwise axis 201 of the first endplate 200. In the illustrated embodiment, the first and second angles $\beta_1$, $\beta_2$ of the first and second sets of openings 230, 250 of the first and second extensions 206, 208 are congruent angles. The first and second sets of openings 230, 250 may define any suitable first and second angles $\beta_1$, $\beta_2$. A skilled artisan will be able to determine suitable first and second angles $\beta_1$, $\beta_2$ for the first and second sets of openings 230, 250 according to a particular example based on various considerations, including the size of a pin passing through each opening, the overall height difference between the first configuration to the second configuration, and other considerations. An example of suitable first and second angles includes an angle of about 45°. Additionally, as illustrated in FIG. 3, the first extension 206 includes a first extension inner surface 235 and a first extension outer surface 237 that lie on the same plane and are parallel to each other, but directly oppose each other. Each opening of the first set of openings 230 of the first extension 206 extends through the entirety of the first extension 206 such that each opening extends from the first extension inner surface 235 to the first extension outer surface 237. Similarly, the second extension 230 includes a second extension inner surface 255 and a second extension outer surface 257 that lie on the same place and are parallel to each other, but directly oppose each other. Each opening of the second set of openings 250 of the second extension 208 extends through the entirety of the second extension 208 such that each opening extends from the second extension inner surface 255 to the second extension outer surface 257.

Each opening of the first and second set of openings 230, 250 of the first and second extensions 206, 208 of the first endplate 200 can have any suitable size, shape, and configuration, and a skilled artisan will be able to select suitable size, shape, and configuration parameters for an opening in a set of openings of a main body of an expandable spacer according to a particular embodiment based on various considerations, including the size of a pin passing through the openings, the overall height difference between the first configuration to the second configuration, and other considerations. Additionally, each opening of the first and second set of openings 230, 250 of the first and second extensions 206, 208 of the first endplate 200 can have any suitable structural configuration. Examples of suitable structural configurations include, but are not limited to, elongated circular shapes, elongated rectangular shapes, ovoid, elliptical, and any other suitable structural configuration. In the illustrated embodiment, each opening of the first and second set of openings 230, 250 of the first and second extensions 206, 208 of the first endplate 200 illustrates an oblong rectangular shape.

Figure 11:
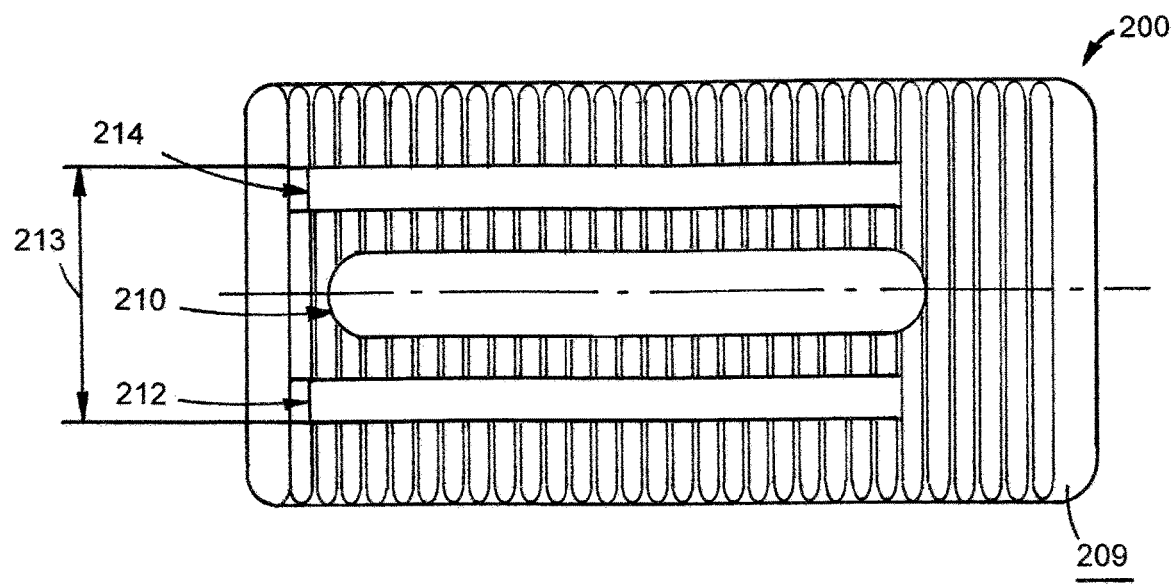
FIG. 11 is a top view of the first endplate of the example expandable spacer illustrated in FIG. 1.

The first endplate 200 also includes a first slot 210, a second slot 212, and a third slot 214. Each of the first, second, and third slots 210, 212, 214 is disposed parallel to the lengthwise axis 201 of the first endplate 200 and extends through the entirety of the first endplate 200 such that each of the first, second, and third slots 210, 212, 214 extends from the first endplate top surface 209 to the first endplate bottom surface 211. As illustrated in FIG. 11, the first slot 210 is positioned on the medial portion of the first endplate 200 such that the first slot 210 is disposed between the first and second extensions 206, 208. The second slot 212 is positioned toward the medial portion of the first endplate 200 but is positioned between the first slot 210 and the first extension 206 of the first endplate 200. The third slot 214 is positioned toward the medial portion of the first endplate 200 but is positioned between the first slot 210 and the second extension 208 of the first endplate 200. In this illustrated embodiment, the second and third slots 212, 214 are positioned at a first width 213 on the first endplate 200. Each of the second and third slots 212, 214 are sized and configured to receive and interface with third and fourth extensions 306, 308 of the second endplate 300, which is described in detail below.

As illustrated in FIG. 8, the second endplate 300 has a second endplate first end 302, a second endplate second end 304, a lengthwise axis 301 extending between the second endplate first end 302 to the second endplate second end 304, a third extension 306, a fourth extension 308, a second endplate top surface 309, and a second endplate bottom surface 311. The second endplate 300 is defined by a length 303 that is measured from the second endplate first end 302 to the second endplate second end 304.

The second endplate top surface 309 and the second endplate bottom surface 311 lie on the same plane but directly oppose each other. As illustrated in FIG. 8, the second endplate top surface 309 defines a second endplate depressed portion 316 that extends from second endplate first end 302 towards the medial portion of the second endplate 300. When the expandable spacer 10 is in its first configuration, the second endplate depressed portion 316 is continuous with the second depressed portion 132 of the main body 100 such that the second endplate depressed portion 316 lies on the same plane as the second depressed portion 132 of the main body 100. The second endplate top surface 309 also defines a set of protruding ridges 318 that extend between the second endplate depressed portion 316 to the second endplate second end 304. Furthermore, as illustrated in FIG. 8, the second endplate bottom surface 311 defines the third and fourth extensions 306, 308 and a second endplate bottom surface notch 320. The second endplate bottom surface notch 320 is disposed on the second endplate second end 304, and the second endplate bottom surface notch 320 is sized and configured to receive and interface with threaded opening 114 of the main body 100 when the expandable spacer 10 is in its first configuration.

The third extension 306 has a third extension first end 332 and a third extension second end 334, and the fourth extension 308 has a fourth extension first end 352 and a fourth extension second end 354. In the illustrated embodiment, the third and fourth extensions 306, 308 of the second endplate 300 extend from the second endplate bottom surface 311 away from the second endplate top surface 309. As illustrated in FIG. 8, the first and second extensions 306, 308 lie on the same plane and are parallel to each other, but directly oppose each other. The third extension 306 includes a third set of openings 330 that are positioned at a third angle $\beta_3$ relative to the lengthwise axis 301 of the second endplate 300. Similarly, the fourth extension 308 includes a fourth set of openings 350 that are positioned at a fourth angle $\beta_4$ relative to the lengthwise axis 301 of the second endplate 300. In the illustrated embodiment, the third and fourth angles $\beta_3$, $\beta_4$ of the third and fourth sets of openings 330, 350 of the third and fourth extensions 306, 308 are congruent angles. The third and fourth sets of openings 330, 350 may define any suitable third and fourth angles $\beta_3$, $\beta_4$. A skilled artisan will be able to determine a suitable third and fourth angles $\beta_3$, $\beta_4$ for the third and fourth sets of openings 330, 350 according to a particular example based on various considerations, including the size of a pin passing through each opening, the overall height difference between the first configuration to the second configuration, and other considerations. An example of suitable first and second angles includes an angle about 45°. Additionally, as illustrated in this embodiment, the third extension 306 includes a third extension inner surface 335 and a third extension outer surface 337 that lie on the same plane and are parallel to each other, but directly oppose each other. Each opening of the third set of openings 330 of the third extension 306 extends through the entirety of the third extension 306 such that each opening extends from the third extension inner surface 335 to the third extension outer surface 337. Similarly, the fourth extension 308 includes a fourth extension inner surface 355 and a fourth extension outer surface 357 that lie on the same place and are parallel to each other, but directly oppose each other. Each opening of the fourth set of openings 350 of the fourth extension 308 extends through the entirety of the fourth extension 308 such that each opening extends from the fourth extension inner surface 355 to the fourth extension outer surface 357.

Each opening of the third and fourth set of openings 330, 350 of the third and fourth extensions 306, 308 of the second endplate 300 can have any suitable size, shape, and configuration, and a skilled artisan will be able to select suitable size, shape, and configuration parameters for an opening in a set of openings of a main body of an expandable spacer according to a particular embodiment based on various considerations, including the size of a pin passing through the openings, the overall height difference between the first configuration to the second configuration, and other considerations. Additionally, each opening of the third and fourth set of openings 330, 350 of the third and fourth extensions 306, 308 of the second endplate 300 can have any suitable structural configuration. Examples of suitable structural configurations include, but are not limited to, elongated circular shapes, elongated rectangular shapes, ovoid, elliptical, and any other suitable structural configuration. In the illustrated embodiment, each opening of the third and fourth set of openings 330, 350 of the third and fourth extensions 306, 308 of the second endplate 300 illustrates an oblong rectangular shape.

The second endplate 300 also includes a fourth slot 310, a fifth slot 312, and a sixth slot 314. Each of the fourth, fifth, and sixth slots 310, 312, 314 is disposed parallel to the lengthwise axis 301 of the second endplate 300 and extends through the entirety of the second endplate 300 such that each of the fourth, fifth, and sixth slots 310, 312, 314 extends from the second endplate top surface 309 to the second endplate bottom surface 311. As illustrated in FIG. 12, the fourth slot 310 is positioned on the medial portion of the second endplate 300 such that the fourth slot 310 is disposed between the third and fourth extensions 306, 308. The fifth slot 312 is positioned toward the medial portion of the second endplate 300 but is not positioned between the fourth slot 310 and the third extension 306 of the second endplate 300. The sixth slot 314 is positioned toward the medial portion of the second endplate 300 but is not positioned between the fourth slot 310 and the fourth extension 308 of the second endplate 200. Additionally, in this illustrated embodiment, the second and third slots 212, 214 are positioned at a second width 313 on the second endplate 300.

Each of the fourth, fifth, and sixth slots 310, 312, 314 are sized and configured to receive and interface with first and second extensions 206, 208 of the first endplate 200.

As illustrated in FIGS. 5 and 6, the driving member 400 has a driving member first end 402, a driving member second end 404, a lengthwise axis 401 extending between the driving member first end 402 to the driving member second end 404, a driving member first lateral wall 406, a driving member second lateral wall 408, a driving member third lateral wall 410, and a driving member fourth lateral wall 412. The driving member first lateral wall 406 has an inner surface 423 and an outer surface 425. The driving member second lateral wall 408 has an inner surface 433 and an opposing outer surface 435. The driving member third lateral wall 410 has an inner surface 443 and an opposing outer surface 445. The driving member fourth lateral wall 112 has an inner surface 453 and an opposing outer surface 455. The inner surfaces 423, 433, 443, 453 of the driving member first lateral wall 406, driving member second lateral wall 408, driving member third lateral wall 410, and driving member fourth lateral wall 412 cooperatively define a driving member interior surface 115 and a driving member interior chamber 416. Similarly, the opposing outer surfaces 425, 435, 445, 455 of the driving member first lateral wall 406, driving member second lateral wall 408, driving member third lateral wall 410, and driving member fourth lateral wall 412 cooperatively define a driving member outer surface 117. Additionally, the driving member 400 is defined by a length 403 that is measured from the driving member first end 402 to the driving member second end 404.

The driving member second end 404 defines the second lateral wall 408 and a driving member channel 430. As best illustrated in FIG. 6, the driving member channel 430 is aligned on a plane perpendicular to the lengthwise axis 401 of the driving member 400. The driving member channel 430 and the driving member interior chamber 416 are separated by the second lateral wall 408 and are not in fluid communication. The driving member channel 430 is sized and configured to mate with a cam 616 of the actuation member 600, which is described in detail below, to allow the expandable spacer 10 to transition from a first configuration to a second configuration when the actuation member 600 is moved towards the driving member interior chamber 416.

As illustrated in FIGS. 5 and 6, the third lateral wall 410 of the driving member 400 has a first set of openings 440, and the fourth lateral wall 412 of the driving member 400 has a second set of openings 450. Each opening of the first set of openings 440 extends entirely through the third lateral wall 410 of the driving member 400 such that each opening extends from the driving member inner surface 415 to the driving member outer surface 417. Similarly, each opening of the second set of openings 450 extends entirely through the fourth lateral wall 412 of the driving member 400 such that each opening extends between the driving member inner surface 415 to the driving member outer surface 417. In the illustrated embodiment, each opening of the first set of openings 440 on the third lateral wall 410 is directly aligned with each opening of the second set of openings 450 on the fourth lateral wall 412 such that the first set of openings 440 and the second set of openings 450 directly oppose each other. Each opening of the first set of openings 440 and the second set of openings 450 is sized and configured to receive a pin from a plurality of pins 500, which is described in detail below. The alignment and the configuration of each opening of the first and second set of openings 440, 450 is considered advantageous at least because a pin from the plurality of pins 500 is able to pass through either the first or second set of openings 440, 450 to connect the main body 100, the first endplate 200, the second endplate 300, and the driving member 400 together in order for the expandable spacer 10 to transition from a first configuration to a second configuration.

Each opening of the first and second set of openings 440, 450 can have any suitable size, shape, and configuration, and a skilled artisan will be able to select suitable size, shape, and configuration parameters for an opening in a set of openings of a main body of an expandable spacer according to a particular embodiment based on various considerations, including the size of a pin passing through the openings, the overall height difference between the first configuration to the second configuration, and other considerations. Additionally, each opening of the first and second set of openings 440, 450 can have any suitable structural configuration. Examples of suitable structural configurations include, but are not limited to, elongated circular shapes, elongated rectangular shapes, ovoid, elliptical, and any other suitable structural configuration. In the illustrated embodiment, each opening of the first and second set of openings 440, 450 illustrates a circular shape.

In FIG. 9, each pin of the plurality of pins 500 has a pin first end 502, a pin second end 504, a lengthwise axis 501 of each pin that extends from the pin first end 502 to the pin second end 504, and a length 503 that is measured from the pin first end 502 to the pin second end 504.

In this illustrated embodiment, each pin from the plurality of pins 500 may be inserted into the expandable spacer 10 either by the pin first end 502 or the pin second end 504. For example, a pin from the plurality of pins 500 may be inserted either by its pin first end 502 or a pin second end 504 into an opening of the first set of openings 170 on the third lateral wall 110 of the main body 100, passes through an opening on the first set of openings 230 on the first extension 206 of the first endplate 200, passes through an opening on the third set of openings 330 on the third extension 306 of the second endplate 300, passes through an opening of the first set of openings 440 of the third lateral wall 410 of the driving member 400, passes through the driving member interior chamber 416, passes through an opening of the second set of openings 450 of the fourth lateral wall 412 of the driving member 400, passes through an opening of the fourth set of openings 350 of the fourth extension 308 of the second endplate 300, passes through an opening of the second set of openings 350 of the second extension 208 of the first endplate 200, and passes through and terminates at an opening of the second set of openings 180 of the fourth lateral wall 112 of the main body 100.

The actuation member 600 has an actuation member first end 602, an actuation member second end 604, a lengthwise axis 601 that extends from the actuation member first end 602 to the actuation member second end 604, a threading 606, a circumferential cam 608, and an actuation member recess 610. The length 603 of the actuation member 600 is measured from the actuation member first end 602 to the actuation member second end 604.

The actuation member first end 602 disposes the circumferential cam 608. As illustrated in FIG. 10, the circumferential cam 608 extends circumferentially around the actuation member outer surface 615 towards the driving member first end 602, and the circumferential cam 608 is sized and configured to interface with the driving member channel 430. In the illustrated embodiment, the circumferential cam 608 is inserted into the driving member channel 430 before the plurality of pins 500 is inserted into the expandable spacer 100 for ease of assembly. Additionally, the circumferential cam 608 is considered advantageous at least because the circumferential cam 608 allows the actuation member 600 to transition the driving member 400 towards the first lateral wall 106 of the main body 100, which, in turn, allows the expandable spacer 10 to transition from a first configuration to a second configuration.

The actuation member second end 604 disposes the actuation member recess 610 that has a series of facets 612 and an actuation member inner surface 613. The actuation member recess 610 extends from the actuation member second end 604 towards the actuation member first end 602. The actuation member recess 610 is sized and configured to receive a driving tool (not illustrated) to assist in rotating and transitioning the actuation member 600 from a first position to a second position such that the expandable spacer 600 transitions from a first configuration to a second configuration. Additionally, the actuation member recess 610 can have any suitable size, shape, and configuration, and a skilled artisan will be able to select suitable size, shape, and configuration parameters for a driving member recess of an expandable spacer according to a particular embodiment based on various considerations, including the size of the driving tool. Additionally, the driving member recess 610 can have any suitable structural configuration. Examples driving member recess considered suitable for a series of facets to define include, but are not limited to, hexagonal, triangular, square, pentagonal, slotted, cross-recesses, Philips, hex socket, Philips-square, or any other driving member recess considered suitable for a particular application. In the illustrated embodiment, the driving member recess 610 illustrates a star-shaped configuration.

The actuation member 600 also defines the threading 606. The threading 606 extends along a portion of the actuation member 600 between the actuation member first end 602 to the actuation member second end 604 and is circumferentially disposed around the portion of the actuation member outer surface 615. The threading 606 is sized and configured to be inserted into the groove 156 of the threaded opening 114 to transition the actuation member 600 from a first position to a second position.

In use, and described in greater detail below, the expandable spacer 10 includes the first and second configurations. Each of the FIGS. 1 and 14 illustrates the expandable spacer 10 in the first, contracted configuration. In the first configuration, the first endplate 200 is in contact with and adjacent to the main body 100 such that the first endplate bottom surface 211 interfaces with the main body top surface 119. Additionally, the first endplate 200 is in contact with and adjacent to the main body 100 such that the first and second extensions are disposed in the main body interior chamber 116, the first extension outer surface 237 and first extension outer surface 257 interface with the main body inner surface 115.

In the first configuration, the first and second extensions 206, 208 of the first endplate 200 dispose inside the fifth and sixth slots 312, 314 of the second endplate 200, but do not contact the fifth or sixth slots 312, 314 of the second endplate 200. As illustrated in FIG. 13, when the expandable spacer 10 is in its first configuration, the first and second extensions 206, 208 of the first endplate 200 are parallel with the second set of protruding ridges 318 of the second endplate 300. Similarly, the third and fourth extensions 306, 308 of the second endplate 300 dispose inside the second and third slots 212, 214 of the first endplate 200, but do not contact the second or third 212, 214 of the first endplate 200. As illustrated in FIG. 13, the third and fourth extensions 306, 308 of the second endplate 300 are parallel with the first set of protruding ridges 218 of the of first endplate 200. Thus, in this configuration, the expandable spacer 10 is measured at a first height 11. This structural configuration is considered advantageous at least because this allows a user, such as a surgeon, to insert an expandable spacer into a narrower intravertebral space to maximize the spacing between vertebral bodies and restore spinal stability.

Furthermore, in the first configuration, the driving member 400 is disposed inside of the main body interior chamber 116 and is connected to the actuation member 600, specifically the circumferential cam 608 interfaces with the driving member channel 430. In addition, a portion of the threading 606 of the actuation member 600 is disposed inside of the threaded opening 150 and connected to the groove 156 of the threaded opening 150.

As illustrated in FIGS. 13 and 14, the plurality of pins 500 contacts and links the main body 100, the first endplate 200, the second endplate 300, and the driving member 400 together. As described above, each pin of the plurality of pins 500 may be inserted into either the first set of openings 170 on the third lateral wall 110 of the main body 100 or the second set of openings 180 on the fourth lateral wall 112 of the main body 100 to link and assemble the expandable spacer 10. A skilled artisan will be able to determine how to suitably configure the expandable spacer according to a particular example based on various considerations, including the anatomy of the spinal column in which it will be implanted and the desirability of the use of a driving member. In example embodiments, the expandable spacer may have one, two, three, or more than three configurations. In example embodiments, the planes may be at obtuse or acute angles relative to one another, or may be parallel to one another.

FIG. 14 illustrates the expandable spacer 10 in its second configuration. In this configuration, a user, such as a surgeon, exerts force onto the actuation member 600 such that the actuation member 600 is rotated clockwise to allow the actuation member 600 to transition from a first position to a second position; the second position relates to movement towards the first lateral wall 106 of the main body 100. This transition of the actuation member 600 cooperatively moves the driving member 400 towards the second position, which, in turn, cooperatively moves the plurality of pins 500 with the driving member 400 to the second position to transition the expandable spacer 10 to its second configuration. The crossing patterns of the first and second sets of openings 230, 250 of the first endplate 200 and the third and fourth sets of openings 330, 350 of the second endplate 300 allow the plurality of pins 500 to extend the first and second endplate 200, 300 away from the main body 100 in opposite directions when a force is applied by the driving member 400 and the actuation member 600. Due to the first, second, third, and fourth angles $\beta_1$, $\beta_2$, $\beta_3$, $\beta_4$ of the first, second, third and fourth set of openings 230, 250, 330, 350 of the first and second endplates 200, 300 being congruent angles, the first and second endplates 200, 300 remain parallel to each other when expanded in the second configuration. When the driving member 400, the plurality of pins 500, and the actuation member 600 cooperatively reach the second position, the expandable spacer 10 is in its second configuration and is measured at a second height 13. In this embodiment, the second height 13 for the second configuration of the expandable spacer 10 is greater than the first height 11 for the first configuration of the expandable spacer 10. In this embodiment, the first height is measured at 8 millimeters and the second height is measured at 13 millimeters. The expandable spacer 10 may have any suitable height for either its first configuration or its second configuration. A skilled artisan will be able to determine a suitable height for the first configuration and the second configuration of the expandable spacer 10 according to a particular example based on various considerations, including the height of the disk space, the height need to maintain stability in the spinal column, and other consideration. Examples of suitable first heights for the first configuration include heights between about 7 millimeters to about 8 millimeters, and examples of suitable second heights for the second configuration includes heights between about 11 millimeters to about 13 millimeters.

In the second configuration, a user, such as a surgeon, will place a material into the expandable spacer 10 to fill in all gaps and spaces inside the expandable spacer 10, such as the driving member interior chamber 416, the main body interior chamber 116, and other suitable positions, to maintain the second configuration and allow for stability in the spinal column. The material used may define any material suitable for the expandable spacer 10. A skilled artisan will be able to determine a suitable material to maintain the second configuration of the expandable spacer 10 according to a particular example based on various considerations, including the overall width of the disk space. Examples of suitable materials for the expandable spacer includes allograft, autograft, or other suitable considerations.

The expandable spacer 10 can be made from any conventional material. A skilled artisan will be able to select suitable materials for each of the main body 100, the first endplate 200, the second endplate 300, the driving member 400, the plurality of pins 500, and the actuation member 600. Examples of conventional materials for an expandable spacer include, but are not limited to, metals, polymeric materials, bone material, and other suitable material for this particular application.

Each of the FIGS. 15, 16, 17, 18, and 19 illustrates another example expandable spacer 20. The expandable spacer 20 is similar to the expandable spacer 10 illustrated in FIGS. 1 through 14 and described above, except as detailed below. The expandable spacer 20 includes a main body 700, a first endplate 800, a second endplate 900, a driving member 1000, a plurality of pins 1100, and an actuation member 1150. The expandable spacer 20 is similar to the expandable spacer 10 such that the expandable spacer 20 is movable between a first configuration and a second configuration. In the first configuration, each of the first endplate 800 and second endplate 900 interfaces with the main body 700. Also, each of the driving member 1000, each pin of the plurality of pins 1100, and the actuation member 1150 is in a first position. In the second configuration, each of the first and second endplates 800, 900 is spaced such that the distance between the first and second endplates 800, 900 has increased as compared to the first configuration. The expandable spacer 20 moves between the first configuration and the second configuration through rotational movement of the actuation member 1150, which forces the driving member 1000 to move linearly along a longitudinal axis of the expandable spacer 20. This linear movement of the driving member 1000 also moves each pin of the plurality of pins 1100, which, as a result of their disposition in respective openings 830, 850, 930, 950 in the respective endplates 800, 900, forces the first and second endplates 800, 900 away from each other in opposing direction along an axis transverse to the longitudinal axis.

The driving member 1000 has a driving member first end 1002, a driving member second end 1004, a driving member first lateral wall 1006, a driving member second lateral wall 1008, a driving member third lateral wall 1010, a driving member fourth lateral wall 1012. The driving member first lateral wall 1006 has an inner surface 1023 and an outer surface 1025. The driving member second lateral wall 1008 has an inner surface 1033 and an opposing outer surface 1035. The driving member third lateral wall 1010 has an inner surface 1043 and an opposing outer surface 1045. The driving member fourth lateral wall 1012 has an inner surface 1053 and an opposing outer surface 1055. The inner surfaces 1023, 1033, 1043, 1053 of the driving member first lateral wall 1006, driving member second lateral wall 1008, driving member third lateral wall 1010, and driving member fourth lateral wall 1012 cooperatively define a driving member interior surface 1015 and a driving member interior chamber 1016. Similarly, the opposing outer surfaces 1025, 1035, 1045, 1055 of the driving member first lateral wall 1006, driving member second lateral wall 1008, driving member third lateral wall 1010, and driving member fourth lateral wall 1012 cooperatively define a driving member outer surface 1017. The driving member 1000 is defined by a length 1003 that is measured from the driving member first end 1002 to the driving member second end 1004.

Figure 17:
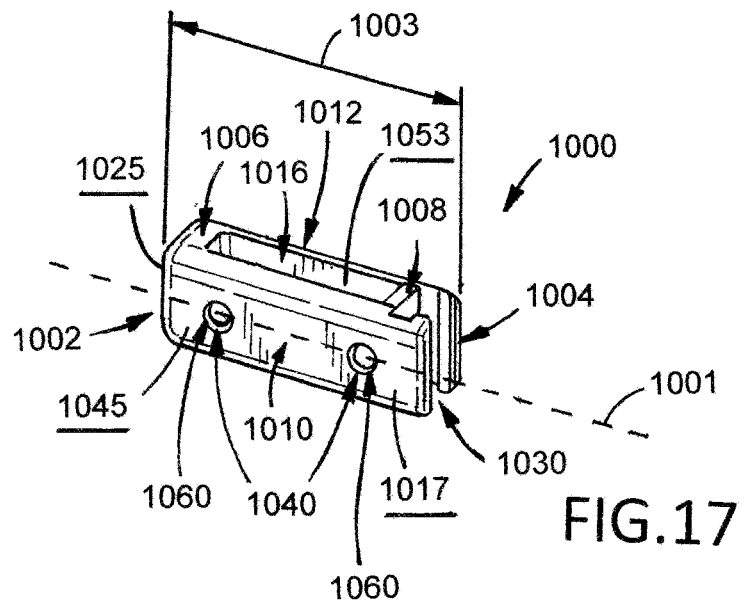
FIG. 17 is a perspective view of the driving member of the example expandable spacer illustrated in FIG. 15.
Figure 18:
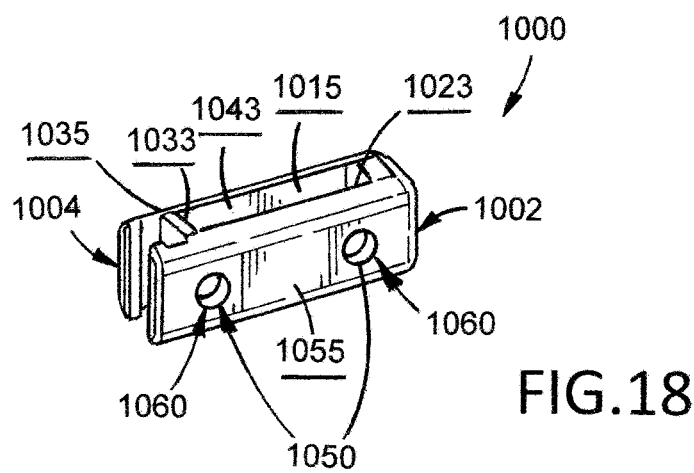
FIG. 18 is a perspective view of the driving member of the example expandable spacer illustrated in FIG. 15.

As illustrated in FIGS. 17 and 18, the driving member third lateral wall 1010 has a first set of openings 1040, and the driving member fourth lateral wall 1012 has a second set of openings 1050. Each opening of the first set of openings 1040 extends entirely through the driving member third lateral wall 1010 such that each opening extends from the driving member inner surface 1015 to the driving member outer surface 1017. Similarly, each opening of the second set of openings 1050 extends entirely through the driving member fourth lateral wall 1012 such that each opening extends between the driving member inner surface 1015 to the driving member outer surface 1017. In the illustrated embodiment, each opening of the first set of openings 1040 on the driving member third lateral wall 1010 is directly aligned with each opening of the second set of openings 450 on the driving member fourth lateral wall 1012 such that the first set of openings 1040 and the second set of openings 1050 directly oppose each other. Each opening of the first set of openings 1040 and the second set of openings 1050 is sized and configured to receive a pin from a plurality of pins 500, which is described in detail below.

However, the driving member third lateral wall 1010 and the fourth lateral wall 1012 has a plurality of attachments members 1060 such that each opening of the first set of openings 1040 and the second set of opening 1050 comprises an attachment member from the plurality of attachment members 1060. In the illustrated embodiment, each attachment member of the plurality of attachments members 1060 is sized and configured to be integrated into each opening of the first set of openings 1040 and the second set of openings 1050. Additionally, each attachment member of the plurality of attachment members 1060 extends entirely through the driving member third and fourth lateral walls 1010, 1012. Thus, each attachment member of the plurality of attachment member 1060 extends from the inner surface 1043 of the driving member third lateral wall 1010 to the outer surface 1045 of the driving member third lateral wall 1010. Similarly, each attachment member of the plurality of attachment member 1060 extends from the inner surface 1053 of the driving member fourth lateral wall 1012 to the outer surface 1055 of the driving member fourth lateral wall 1012.

Figure 19:
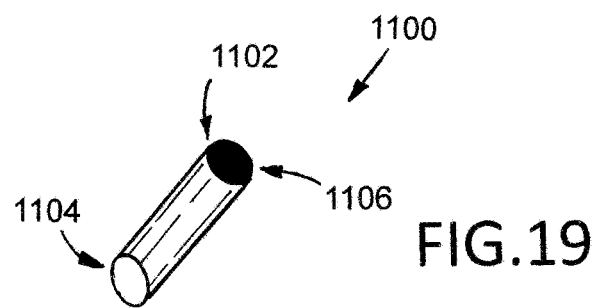
FIG. 19 is a perspective view of a pin of the plurality of pins of the example expandable spacer illustrated in FIG. 15.

In FIG. 19, each pin of the plurality of pins 1100 defines a pin first end 1102, a pin second end 1104, a lengthwise axis 1101 of each pin that extends from the pin first end 1102 to the pin second end 1104, and a length 1103 that is measured from the pin first end 1102 to the pin second end 1104.

As illustrated in the embodiment, the pin first end 1102 for each pin of the plurality of pins 1100 defines a fitting 1106 that is sized and configured to attach to an attachment member from the plurality of attachment members 1160 disposed on the driving member 1000. For the expandable spacer 20, the pin first end 1102 for each pin of the plurality of pins 1100 enters and passes through the main body 700, the first endplate 800, the second endplate 900, and the driving member 1000 in a similar way as described in the expandable spacer 10 for the main body 100, the first endplate 200, the second endplate 300, and the driving member 400. However, in this embodiment, the pin first end 1102 for each pin of the plurality of pins 1100 terminates at the driving member 1000 such that the fitting 1106 for each pin of the plurality pins 1100 releasably attaches to each attachment member of the plurality of attachment members 1060. In this embodiment, the plurality of pins 1100 includes at least two pins and the plurality of attachment members 1060 includes at least two attachment members on the driving member 1000.

The attachment arrangement between plurality of attachment members 1060 and the plurality of pins 1100 is considered advantageous at least because the expandable spacer 20 can be readily assembled or disassembled in order to connect and disconnect the main body 700, the first endplate 800, and second endplate 900, and the driving member 1000 together to allow the expandable spacer 20 to transition from a first configuration to a second configuration. A skilled artisan will be able to select suitable attachment arrangements for attaching the plurality of pins 1100 to the plurality of attachment members 1060. Example attachment arrangements considered suitable for attaching the plurality of pins 1100 to the plurality of attachment member 1060 include, but not limited to, affixing the plurality of pins to the plurality of the attachment members, securing the plurality of pins to the plurality of attachment members, connecting the plurality of pins to the plurality of attachment members, locking the plurality of pins to the plurality of attachment members, fastening the plurality of pins to the plurality of attachment members, and any other attachment arrangement considered suitable for a particular application. Furthermore, once the plurality of pins 1100 is received and attached to the plurality of attachment member 1060, the plurality of pins 1100 terminates into the plurality of the attachment member 1060 and does not enter or pass through the driving member interior chamber 1016. The exclusion of the plurality of pins 1100 from entering or passing through the driving member interior chamber 1016 is considered advantageous at least because a user, such as a surgeon, can fill the driving member interior chamber 1016 with a suitable material, such as bone material, to allow an expandable spacer to maintain its second configuration when placed in a patient.

Figure 20:
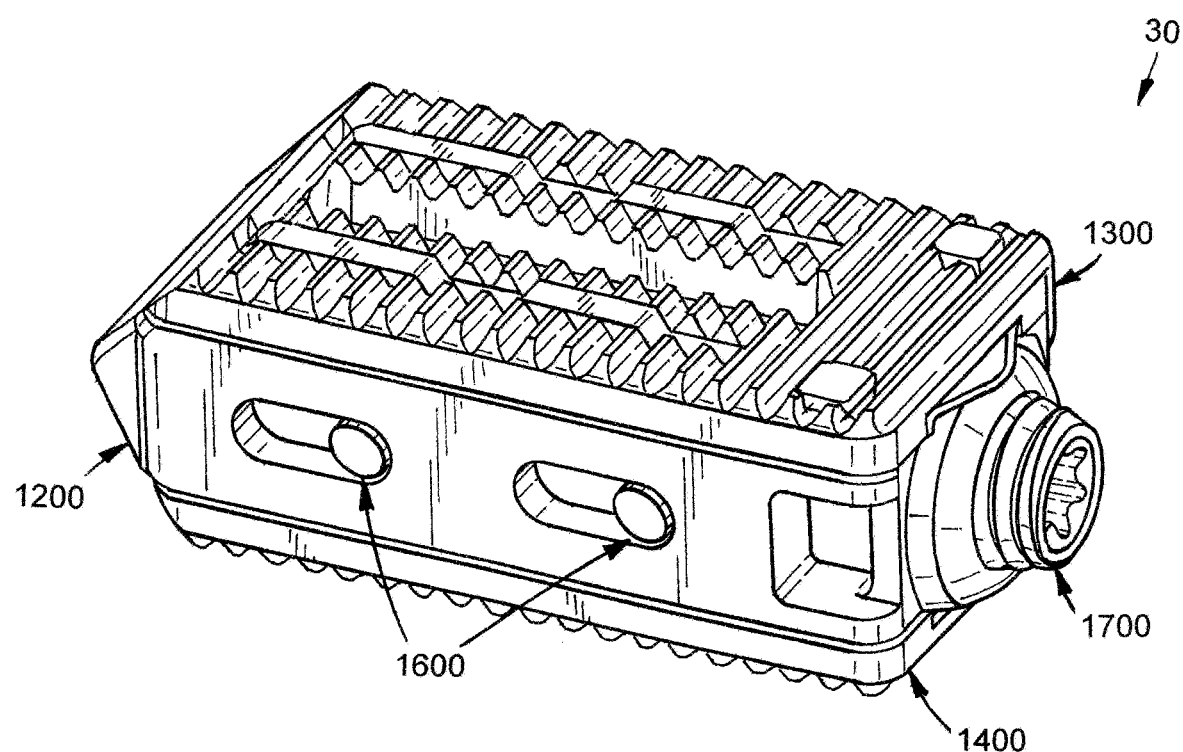
FIG. 20 is a perspective view of another example expandable spacer.
Figure 21:
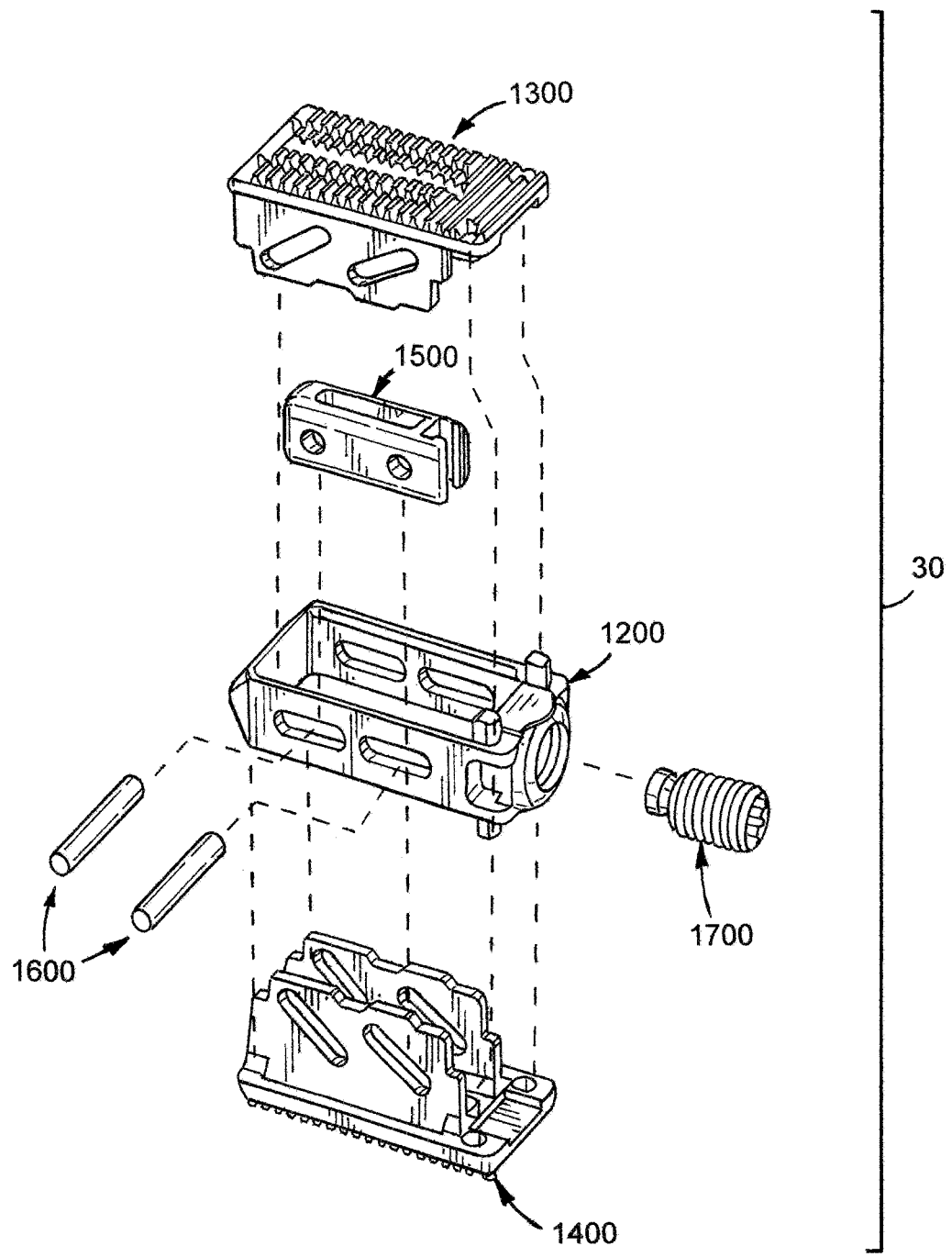
FIG. 21 is an exploded view of the example expandable spacer illustrated in FIG. 20.
Figure 28:
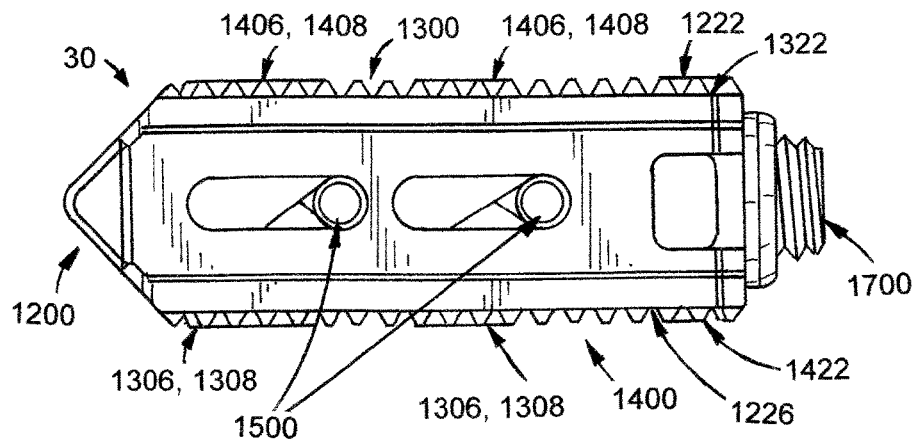
FIG. 28 is a side view of the example expandable spacer illustrated in FIG. 20. The expandable spacer is shown in the first configuration.
Figure 29:
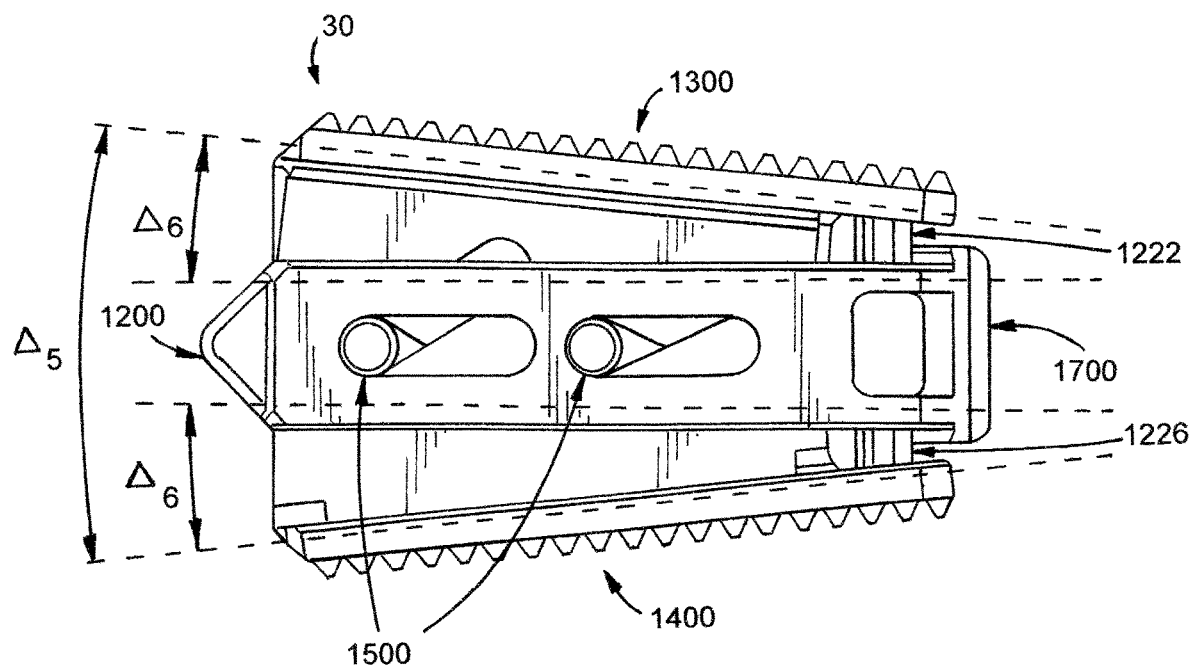
FIG. 29 is a side view of the example expandable spacer illustrated in FIG. 20. The expandable spacer is shown in the second configuration.

Each of the FIGS. 20, 21, 22, 23, 24, 25, 26, 27, 28, and 29 illustrates another example expandable spacer 30. The expandable spacer 30 is similar to the expandable spacer 10 illustrated in FIGS. 1 through 14 and described above, except as detailed below. The expandable spacer 30 includes a main body 1200, a first endplate 1300, a second endplate 1400, a driving member 1500, a plurality of pins 1600, and an actuation member 1700. The expandable spacer 30 is movable between a first configuration and a second configuration. In the first configuration, as illustrated in FIGS. 20 and 28, each of the first endplate 1300 and second endplate 1400 interfaces with the main body 1200. Also, each of the driving member 1500, each pin of the plurality of pins 1600, and the actuation member 1700 is in a first position. In the second configuration, as illustrated in FIG. 29, each of the first and second endplates 1300, 1400 is spaced such that the distance between the first and second endplates 1300, 1400 has increased as compared to the first configuration. The expandable spacer 30 moves between the first configuration and the second configuration through rotational movement of the actuation member 1700, which forces the driving member 1500 to move linearly along a longitudinal axis of the expandable spacer 30. This linear movement of the driving member 1500 also moves each pin of the plurality of pins 1600, which, as a result of their disposition in respective openings 1330, 1332, 1350, 1352, 1430, 1432, 1450, 1452 in the respective endplates 1300, 1400, forces the first and second endplates 1300, 1400 away from each other at an angle relative to the longitudinal axis of the expandable spacer 30.

The main body 1200 has a main body first end 1202, a main body second end 1204, a lengthwise axis 1201 extending between the main body first end 1202 to the main body second end 1204, a main body first lateral wall 1206, a main body second lateral wall 1208, a main body third lateral wall 1210, a main body fourth lateral wall 1212, and a threaded opening 1214, a main body inner surface 1215, a main body outer surface 1217, a main body top surface 1219, a main body bottom surface 1221, a first height 1223. The main body first lateral wall 1206 has an upper surface 1231, an opposing lower surface 1233, an inner surface 1235, and an opposing outer surface 1237. The main body second lateral wall 1208 has an upper surface 1251, an opposing lower surface 1253, an inner surface 1255, and an opposing outer surface 1257. The main body third lateral wall 1210 has an upper surface 1271, an opposing lower surface 1273, an inner surface 1275, and an opposing outer surface 1277. The main body fourth lateral wall 1212 has an upper surface 1281, an opposing lower surface 1283, an inner surface 1285, and an opposing outer surface 1287. The inner surfaces 1235, 1255, 1275, 1285 of the main body first lateral wall 1206, main body second lateral wall 1208, main body third lateral wall 1210, and main body fourth lateral wall 1212 cooperatively define a main body interior chamber 1216. Similarly, the opposing outer surfaces 1237, 1257, 1277, 1287 of the main body first lateral wall 1206, main body second lateral wall 1208, main body third lateral wall 1210, and main body fourth lateral wall 1212 cooperatively define a main body outer surface 1217. The upper surfaces 1231, 1251, 1271, 1281 of the main body first lateral wall 1206, main body second lateral wall 1208, main body third lateral wall 1210, and main body fourth lateral wall 1212 cooperatively define a main body upper surface 1219. Similarly, the opposing lower surfaces 1233, 1253, 1275, 1285 of the main body first lateral wall 1206, main body second lateral wall 1208, main body third lateral wall 1210, and main body fourth lateral wall 1212 cooperatively define a main body lower surface 1221. Additionally, the main body 1200 is defined by a length 1203 that is measured from the main body first end 1202 to the main body second end 1204.

Figure 24:
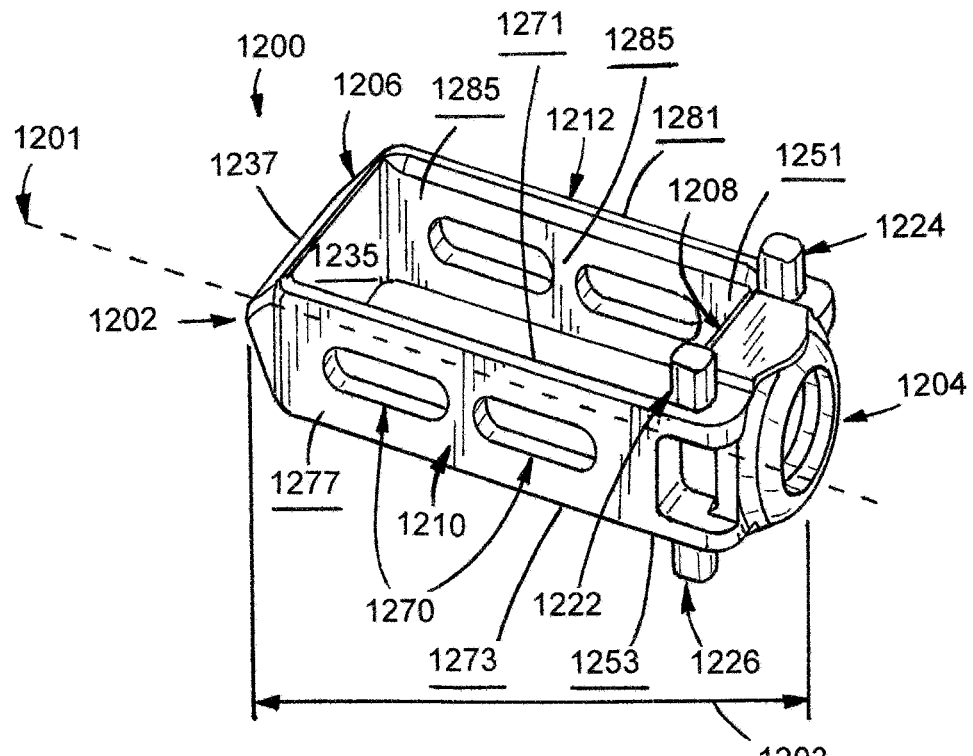
FIG. 24 is a perspective view of the main body of the example expandable spacer illustrated in FIG. 20.
Figure 25:
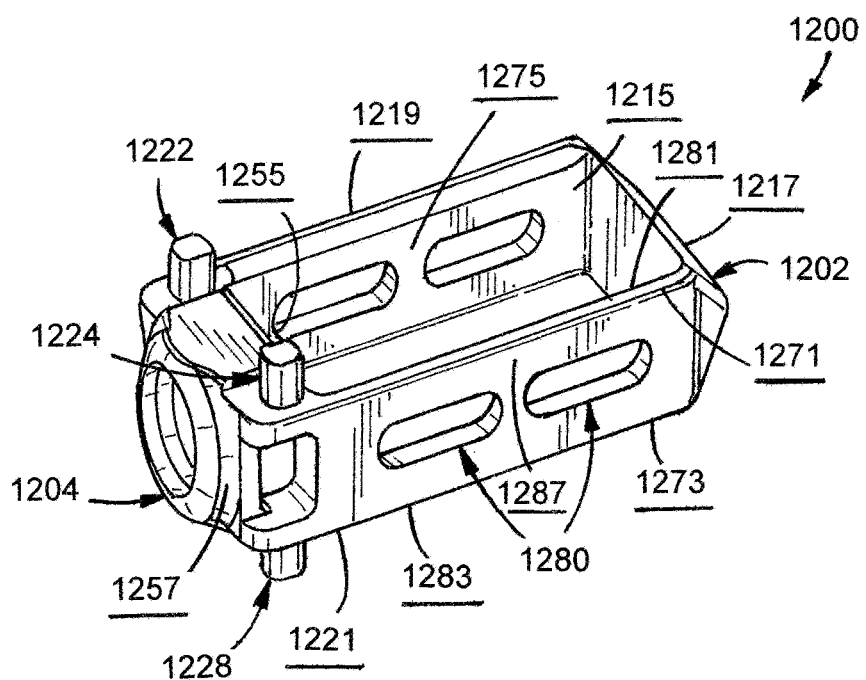
FIG. 25 is a perspective view of the main body of the example expandable spacer illustrated in FIG. 20.
Figure 26:
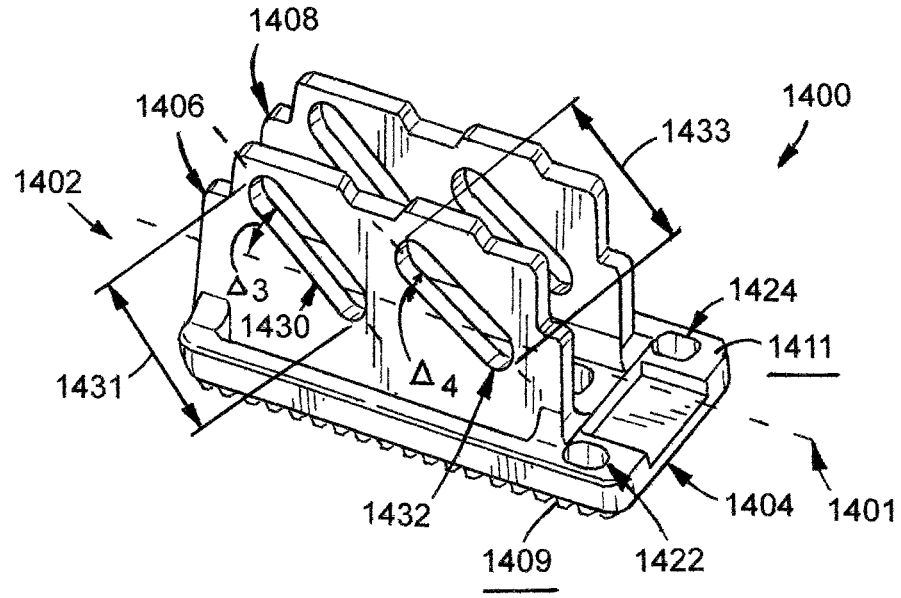
FIG. 26 is a perspective view of the second endplate of the example expandable spacer illustrated in FIG. 20.
Figure 27:
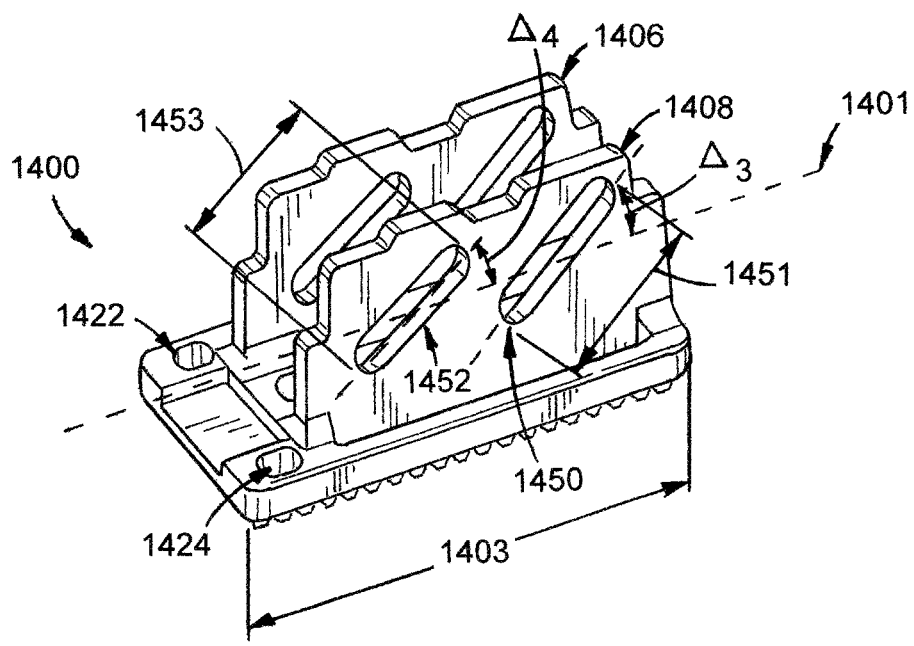
FIG. 27 is a perspective view of the second endplate of the example expandable spacer illustrated in FIG. 20.

In FIGS. 24 and 25, the main body upper surface 1219 has a first support member 1222 and a second support member 1224 that are disposed towards the main body second end 1204. The first and second support members 1222, 1224 are directly adjacent to each other such that the first support member 1222 is disposed on third lateral upper surface 1271 extending away from the main body 1200, and the second support member is disposed on fourth lateral upper surface 1281 extending away from the main body 1200. Additionally, the main body opposing lower surface 1221 has a third support member 1226 and a fourth support member 1228 that are disposed towards the main body second end 1204. The third and fourth support members 1226, 1228 are directly adjacent to each other such that the third support member 1226 is disposed on third lateral lower surface 1283 extending away from the main body 1200, and the fourth support member 1228 is disposed on the fourth lower surface 1285 extending away from the main body 1200. In the illustrated embodiment, the first and third support members 1222, 1226 directly oppose each other, and the second and fourth support member 1224 directly oppose each other. Each of the first, second, third, and fourth support members 1222, 1224, 1226, 1228 is aligned perpendicular to the main body 1200 relative to the lengthwise axis of the main body 1201.

In the illustrated embodiment, the main body third lateral wall 1210 has a main body first set of openings 1270, and the main body fourth lateral wall 1212 has a main body second set of openings 1280. The expandable spacer 30 retains similar structural arrangements as discussed and illustrated previously in the expandable spacer 10. However, each opening of the main body first set of openings 1270 has first opening length 1271, and each opening of the main body second set of openings 1280 has a second opening length 1281. The first and second opening lengths 1271, 1281 for the main body first and second set of openings 1270, 1280 is measured between the main body first end 1202 and the medial portion of the main body 1200 or between the main body second end 1204 and the medial portion of the main body 1200. Additionally, the first and second openings lengths 1271, 1281 of the expandable spacer 30 are greater than the first and second openings lengths 179, 189 of the expandable spacer 10.

Each opening of the main body first and second set of openings 1270, 1280 can have any suitable size, shape, and configuration, and a skilled artisan will be able to select suitable size, shape, and configuration parameters for an opening in a main body set of openings of an expandable spacer according to a particular embodiment based on various considerations, including the size of a pin passing through the openings, the overall height difference between the first configuration to the second configuration, and other considerations. Additionally, each opening of the main body first and second set of openings 1270, 1280 can have any suitable structural configuration. Examples of suitable structural configurations include, but are not limited to, elongated circular shapes, elongated rectangular shapes, ovoid, elliptical, and any other suitable structural configuration. In the illustrated embodiment, each opening of the main body first and second set of openings 1270, 1280 illustrates an oblong rectangular shape.

The first endplate 1300 has a first endplate first end 1302, a first endplate second end 1304, a lengthwise axis 1301 extending between the first endplate first end 1302 to the first endplate second end 1304, a first extension 1306, a second extension 1308, a first endplate top surface 1309, and a first endplate bottom surface 1311. The first endplate 1300 is also defined by a length 1303 that is measured from the first endplate first end 1302 to the first endplate second end 1304.

The first endplate 1300 defines a first support aperture 1322 and a second support aperture 1324 disposed towards the first endplate second end 1304. Each of the first and second support apertures 1323, 1324 extends through the entirety of the first endplate 1300 such that each of the first and second support apertures 1322, 1324 extend from the first endplate top surface 1309 to the first endplate bottom surface 1311. In this illustrated embodiment, the first and second support apertures 1322, 1324 are substantially adjacent to each other due to the first support aperture 1322 positioned towards the first extension 1306 and the second support aperture 1324 positioned towards the second extension 1308. Additionally, the first and second support apertures 1322, 1324 are sized and configured to receive and interface with the first and second support members 1222, 1224 on the main body 1200.

Figure 22:
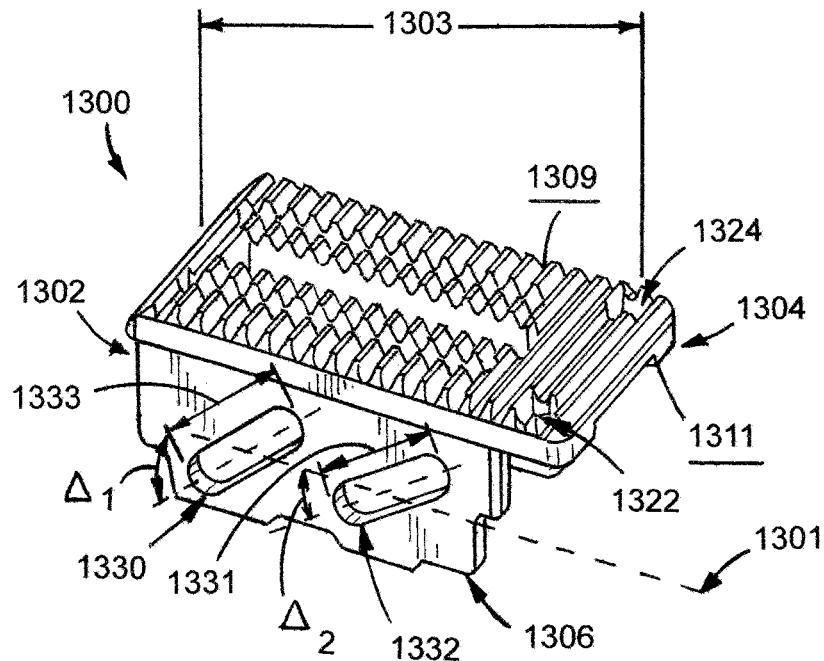
FIG. 22 is a perspective view of the first endplate of the example expandable spacer illustrated in FIG. 20.
Figure 23:
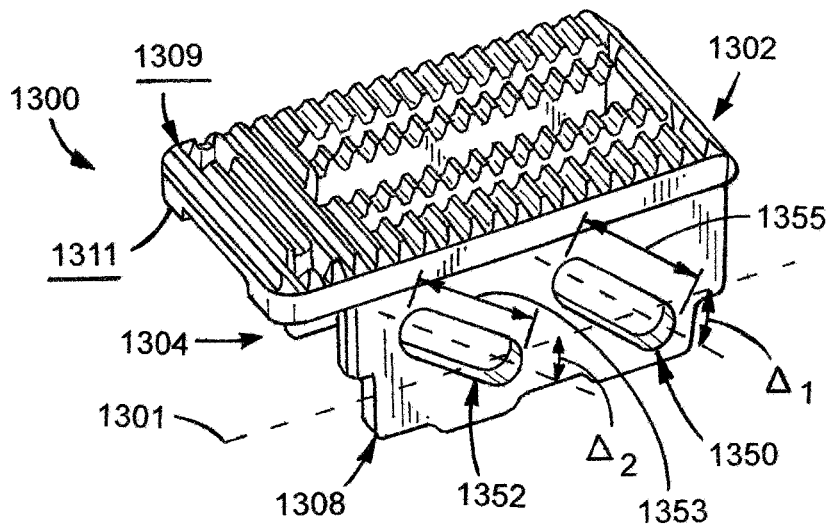
FIG. 23 is a perspective view of the first endplate of the example expandable spacer illustrated in FIG. 20.

In FIGS. 22 and 23, the first extension 1306 of the first endplate 1300 has a first opening 1330 and a second opening 1332, and the second extension 1308 of the first endplate 1300 has a third opening 1350 and a fourth opening 1352. The first and third openings 1330, 1350 of the first and second extensions 1306, 1308 are positioned at a first angle $\Delta_1$ relative to the lengthwise axis 1301 of the first endplate 1300. Similarly, the second and fourth openings 1332, 1352 of the first and second extensions 1306, 1308 are positioned at a second angle $\Delta_2$ relative to the lengthwise axis 1301 of the first endplate 1300. In this illustrated embodiment, the first angle $\Delta_1$ is greater than the second angle $\Delta_2$. The first and third openings 1330, 1350 may define any suitable first angle $\Delta_1$. A skilled artisan will be able to determine a suitable first angle $\Delta_1$ for the first and third openings 1330, 1350 according to a particular example based on various considerations, including the angle of the lordosis present in a patient. An example of suitable first angle includes an angle of about 38°. Additionally, second and fourth openings 1332, 1352 may define any suitable second angle $\Delta_2$. A skilled artisan will be able to determine a suitable second angle $\Delta_2$ for the second and fourth openings 1332, 1352 according to a particular example based on various considerations, including the angle of the lordosis present in a patient. An example of suitable second angle includes an angle of about 30°.

In the illustrated embodiment, the first opening 1330 of the first extension 1306 has a first opening length 1331, and the second opening 1332 of the first extension 1308 has a second opening length 1333. Additionally, the third opening 1350 of the second extension 1308 has a third opening length 1351, and the fourth opening 1352 of the second extension 1308 has a fourth opening length 1353. As illustrated, the second opening length 1333 is greater than the first opening length 1331, and the fourth opening length 1353 is greater than the third opening length 1351. Additionally, the first opening length 1331 and the third opening length 1351 are equal, and the second opening length 1333 and the fourth opening length 1353 are equal. Each of the first, second, third and fourth opening lengths 1331, 1333, 1351, 1353 are measured between the first endplate first end 1302 and the medial portion of the first endplate 1300 or between the first endplate second end 1304 and the medial portion of the first endplate 1300.

The second endplate 1400 has a second endplate first end 1402, a second endplate second end 1404, a lengthwise axis 1401 extending between the second endplate first end 1402 to the second endplate second end 1404, a third extension 1406, a fourth extension 1408, a second endplate top surface 1409, and a second endplate bottom surface 1411. The second endplate 1400 is also defined by a length 1403 that is measured from the second endplate first end 1402 to the second endplate second end 1404.

The second endplate 1400 defines a third support aperture 1422 and a fourth support aperture 1424 disposed towards the second endplate second end 1404. Each of the third and fourth support apertures 1422, 1424 extends through the entirety of the second endplate 1400 such that each of the third and fourth support apertures 1422, 1424 extend from the second endplate top surface 1409 to the second endplate bottom surface 1411. In the illustrated embodiment, the third and fourth support apertures 1422, 1424 are substantially adjacent to each other due to the third support aperture 1422 positioned towards the third extension 1406 of the second endplate 1400 and the second support aperture 1424 positioned towards the fourth extension 1408 of the second endplate 1400. Additionally, the third and fourth support apertures 1422, 1424 are sized and configured to receive and interface with the third and fourth support members 1226, 1228 on the main body 1200.

The first extension 1406 of the second endplate 1400 has a first opening 1430 and a second opening 1432, and the fourth extension 1408 of the second endplate 1400 has a third opening 1450 and a fourth opening 1452. The first and third openings 1430, 1450 of the third and fourth extensions 1406, 1408 are positioned at a third angle $\Delta_3$ relative to the lengthwise axis 1401 of the first endplate 1400. Similarly, the second and fourth openings 1432, 1452 of the first and second extensions 1406, 1408 are positioned at a fourth angle $\Delta_4$ relative to the lengthwise axis 1401 of the first endplate 1400. In this illustrated embodiment, the third angle $\Delta_3$ is greater than the fourth angle $\Delta_4$. The first and third openings 1430, 1450 may define any suitable third angle $\Delta_3$. A skilled artisan will be able to determine a suitable third angle $\Delta_3$ for the first and third openings 1430, 1450 according to a particular example based on various considerations, including the angle of the lordosis present in a patient. An example of suitable third angle includes an angle of about 38°. Additionally, second and fourth openings 1432, 1452 may define any suitable fourth angle $\Delta_4$. A skilled artisan will be able to determine a suitable fourth angle $\Delta_4$ for the second and fourth openings 1432, 1452 according to a particular example based on various considerations, including the angle of the lordosis present in a patient. An example of suitable fourth angle includes an angle of about 30°.

In the illustrated embodiment, the first opening 1430 of the third extension 1406 has a first opening length 1431, and the second opening 1432 of the third extension 1408 has a second opening length 1433. Additionally, the third opening 1450 of the fourth extension 1408 has a third opening length 1451, and the fourth opening 1452 of the fourth extension 1408 has a fourth opening length 1453. In the illustrated embodiment, the second opening length 1433 is greater than the first opening length 1431, and the fourth opening length 1453 is greater than the third opening length 1451. Additionally, the first opening length 1431 and the third opening length 1451 are equal, and the second opening length 1433 and the fourth opening length 1453 are equal. Each of the first, second, third and fourth opening lengths 1431, 1433, 1451, 1453 are measured between the second endplate first end 1402 and the medial portion of the second endplate 1400 or between the second endplate second end 1404 and the medial portion of the second endplate 1400.

In the illustrated embodiment, the first angle $\Delta_1$ of the first and third openings 1330, 1350 of the first endplate 1300 is congruent to the third angle $\Delta_3$ of the first and third openings 1430, 1450 of the second endplate 1400. Similarly, the second angle $\Delta_2$ of the second and fourth openings 1332, 1352 of the first endplate 1300 is congruent to the fourth angle $\Delta_4$ of the second and fourth openings 1432, 1452 of the second opening 1400. This configuration for each of the first, second, third, and fourth angles $\Delta_1$, $\Delta_2$, $\Delta_3$, $\Delta_4$ is considered advantageous at least because the first, second, third, and fourth angles $\Delta_1$, $\Delta_2$, $\Delta_3$, $\Delta_4$ allow the first and second endplates 1300, 1400 to pivot away from the main body 1200. The first endplate 1300 pivots away from the main body 1200 at a fifth angle $\Delta_5$ defined by the lengthwise axis of the main body 1200. Similarly, the second endplate 1400 pivots away from the main body 1200 at a sixth angle $\Delta_6$ defined by the lengthwise axis of the main 1200. A skilled artisan will be able to determine a suitable fifth angle $\Delta_5$ for the expandable spacer 30 according to a particular example based on various considerations, including the angle of the lordosis present in a patient. An example of suitable fifth angle includes an angle of about 12°.

In use, the first and second support members 1222, 1224 are positioned inside of the first and second support apertures 1322, 1324 when the expandable spacer 30 is in its first configuration such that the first support member 1222 is positioned inside of the first support aperture 1322 and the second support member 1224 is positioned inside of the second support aperture 1324. Similarly, the third and fourth support members 1226, 1228 are positioned inside of the third and fourth support apertures 1422, 1424 when the expandable spacer 30 is in its first configuration such that the third support member 1226 is positioned inside of the third support aperture 1422 and the fourth support member 1228 is positioned inside of the second support aperture 1424. Once the actuation member 1700 transitions from the main body first end 1202 to the main body second end 1204 by a user to allow the expandable spacer 30 to transition from its first configuration to its second configuration, the first and second support members 1222, 1224 interface with the first and second support apertures 1322, 1324 to guide the first endplate 1300 from the first configuration to the second configuration, and the third and fourth support members 1226, 1228 interface with the third and fourth support apertures 1422, 1424 to guide the second endplate 1400 from the first configuration to the second configuration. Once both the first and second endplates 1300, 1400 are in the second configuration, each of the first and second endplates 1300, 1400 interface with a vertebral body to correct lordosis in the patient.

Figure 30:
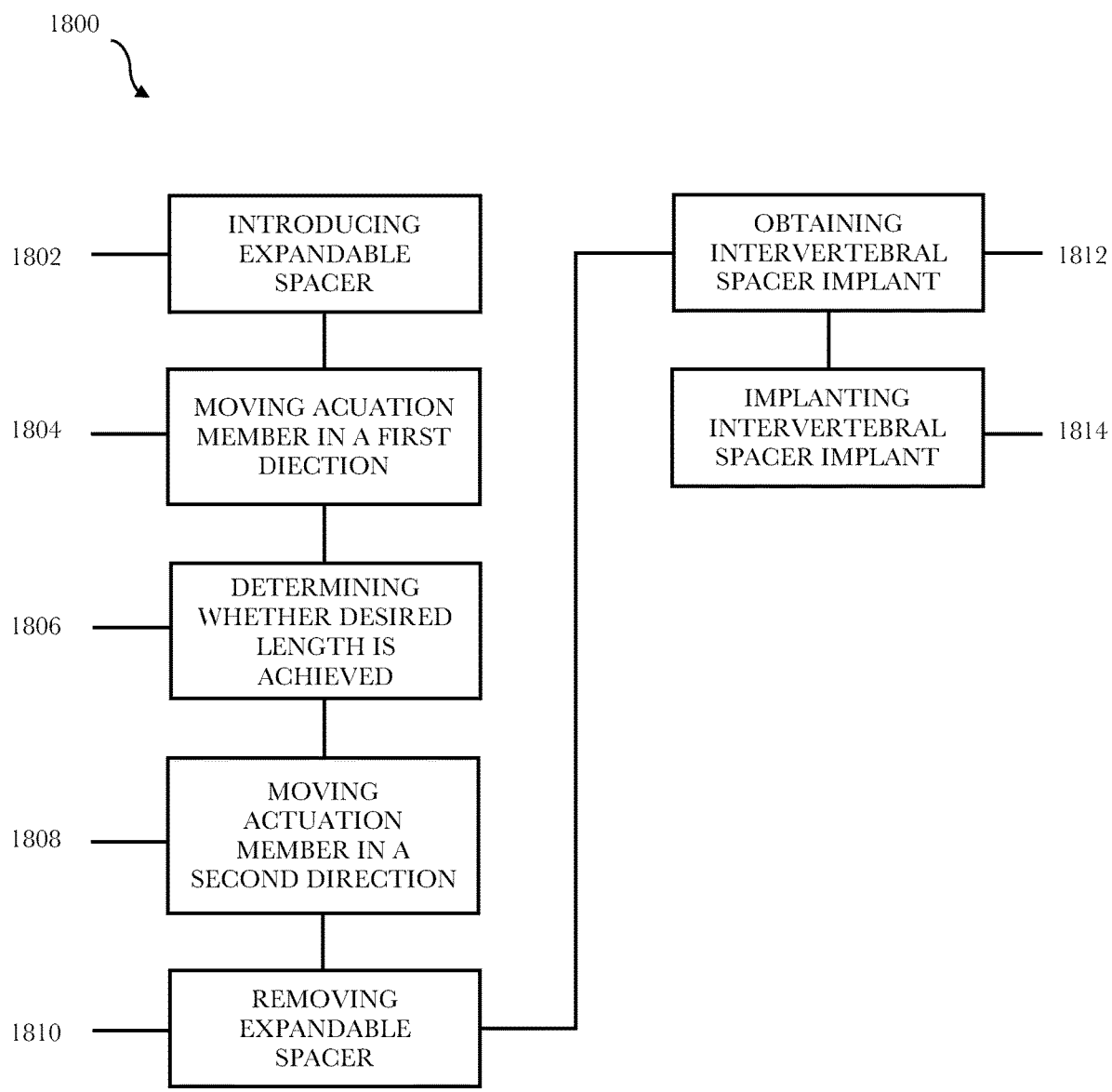
FIG. 30 is a flowchart representation of an example method of sizing an intervertebral spacer implant.

FIG. 30 is a flowchart representation of an example method 1800 of sizing an intervertebral spacer implant between a first vertebra and a second vertebra with an expandable spacer. The initial step 1802 comprises introducing an expandable spacer into a space between a first vertebra and a second vertebra of a patient's vertebrate spinal column. Another step 1804 comprises moving an actuation member in a first direction such that the expandable spacer transitions from a first configuration to a second configuration and interfaces with each of the first vertebra and the second vertebra. Another step 1806 comprises determining whether a desired length is achieved between the first vertebra and the second vertebra. Another step 1808 comprises moving the actuation member in a second direction such that the expandable spacer transitions from the second configuration to the first configuration. Another step 1810 comprises removing the expandable spacer from the space between the first vertebra and the second vertebra. Another step 1812 comprises obtaining an intervertebral spacer implant. Another step 1814 comprises implanting the intervertebral spacer implant between the first vertebra and the second vertebra.

The step 1802 of introducing an expandable spacer into a space between the first vertebra and the second vertebra of the patient's vertebrate spinal column can be accomplished using an expandable spacer according to any embodiment. Skilled artisans will be able to select a suitable expandable spacer according to a particular embodiment based on various considerations, including the degree of curvature of a patient's vertebrate spinal column. Examples of expandable spacers considered suitable to complete step 1802 include expandable spacer 10, expandable spacer 20, expandable spacer 30, and other suitable expandable spacers.

The step 1804 of moving an actuation member in a first direction such that an expandable spacer transitions from a first configuration to a second configuration and interfaces with each of the first vertebra and the second vertebra can be accomplished by a user introducing a driving tool to assist in rotating and transitioning the actuation member from a first position to a second position. In this step, the user applies a force on the driving tool directed toward an actuation member recess such that the driving tool is inserted into the actuation member recess and interfaces with a series of facets. Once the driving tool is inserted into the driving member recess and interfaces with the series of facets, the user applies a rotational force in a first direction on the driving tool until the actuation member transitions from a first position to a second position. The transition of the actuation member from the first position to the second position simultaneously transitions a first endplate, a second endplate, a driving member, and each pin of the plurality of pins from a first position to a second position. Furthermore, step 1804 can be accomplished by using an actuation member according to any embodiment. Skilled artisans will be able to select a suitable actuation member according to a particular embodiment based on various considerations, including the degree of curvature of a patient's vertebrate spinal column. Examples of actuation members considered suitable to complete step 1804 include actuation member 600 of expandable spacer 10, actuation member 1150 of expandable spacer 20, actuation member 1700 of expandable spacer 30, and other suitable actuation members.

The step 1806 of determining whether a desired length is achieved between the first vertebra and the second vertebra can be accomplished by reviewing the length between the first vertebra and the second vertebra once the expandable spacer has transitioned from the first configuration to the second configuration.

The step 1808 of moving the actuation member in a second direction such that the expandable spacer transitions from the second configuration to the first configuration can be accomplished by the user applying a rotational force in a second direction on the driving tool until the actuation member transitions from the second position to the first position. The transition of the actuation member from the second position to the first position simultaneously transitions each of the first endplate, the second endplate, the driving member, and each pin of the plurality of pins from the second position to the first position.

The step 1810 of removing the expandable spacer from the space between the first vertebra and the second vertebra can be accomplished by the user applying a force on the expandable spacer directed away from the patient until the expandable spacer is removed from the patient's vertebrate spinal column.

The step 1812 of obtaining an intervertebral spacer implant can be accomplished by using any intervertebral spacer implant considered suitable for a particular embodiment. For example, step 1812 can be accomplished by selecting an intervertebral spacer implant that correlates with the desired length between a first vertebra and a second vertebra accomplished in step 1806.

The step 1814 of implanting the intervertebral spacer implant between the first vertebra and the second vertebra can be accomplished by using any suitable technique or method of implanting an intervertebral spacer implant within the patient's vertebrate spinal column between the first vertebra and the second vertebra. For example, step 1814 can be accomplished by applying a force on the intervertebral spacer implant directed toward the patient's vertebrate spinal column until the intervertebral spacer implant is disposed in the space between the first vertebra and the second vertebra.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventors simply to describe and illustrate examples of the invention and are not intended to limit the scope of the invention or its protection, which is to be given the full breadth of the appended claims and any and all equivalents thereof.

We claim:

1. An expandable intervertebral spacer having a first configuration and a second configuration, comprising:
    a main body having a main body first lateral wall, a main body second lateral wall having a threaded opening, a main body inner surface, a main body outer surface, a main body third lateral wall connecting the main body first lateral wall to the main body second lateral wall and including at least one opening extending entirely through the main body third lateral wall, a main body fourth lateral wall connecting the main body first lateral wall to the main body second lateral wall and including at least one opening extending entirely through the main body fourth lateral wall, the main body first lateral wall, the main body second lateral wall, the main body third lateral wall, and the main body fourth lateral wall defining a main body interior chamber;
    a first endplate having a first endplate first end, a first endplate second end, a first endplate inner surface, a first endplate outer surface, at least one first endplate slot extending between the first endplate inner surface and the first endplate outer surface, and at least one first endplate extension extending from the first endplate inner surface towards the main body and including at least one opening;
    a second endplate having a second endplate first end, a second endplate second end, a second endplate inner surface, a second endplate outer surface, at least one second endplate slot extending between the second endplate inner surface to the second endplate outer surface, and at least one second endplate extension extending from the second endplate inner surface towards the main body and including at least one opening;
    a driving member disposed within the main body interior cavity and comprising a driving member first lateral wall, a driving member second lateral wall, a driving member third lateral wall, and a driving member fourth lateral wall, the driving member second lateral wall having a channel that is disposed on a plane parallel to the driving member second lateral wall, the driving member third lateral wall disposes at least one opening extending entirely through the driving member third lateral wall, the driving member fourth lateral wall disposes at least one opening extending entirely through the driving member fourth lateral wall;
    an actuation member configured to be inserted into the threaded opening and defines a cam to interface with the channel of the driving member to transition the expandable spacer from the first configuration to the second configuration; and
    a plurality of pins, each pin having a first end and a second end,
        wherein the first end or the second end of each pin is passed through and received by one opening disposed on the main body, one opening disposed on the first endplate, one opening disposed on the second endplate, and one opening disposed on the driving member to assemble the main body, the first endplate, the second endplate, and the driving member together.

2. The expandable spacer of claim 1, wherein the driving member comprises a driving member interior chamber that is free and unobstructed.

3. The expandable spacer of claim 1, wherein at least one extension of the first endplate is disposed inside at least one slot of the second endplate when the expandable spacer is in the first configuration; and
    wherein the extension of the first endplate is parallel to the second endplate outer surface.

4. The expandable spacer of claim 1, wherein at least one extension of the second endplate is disposed inside at least one slot of the first endplate when the expandable is in the first configuration; and
    wherein the extension of the second endplate is parallel to the first endplate outer surface.

5. The expandable spacer of claim 1, wherein the threaded opening is in fluid communication with the main body interior chamber.

6. The expandable spacer of claim 1, wherein at least one opening of the first endplate extension is measured at a first angle and at least one opening of the second endplate extension is measured at a second angle; and
    wherein the first and second angles are congruent angles.

7. The expandable spacer of claim 1, wherein the expandable spacer comprises a first height between the first and second endplates in the first configuration and second height between the first and second endplates in the second configuration; and
    wherein the second height in greater than the first height.

8. The expandable spacer of claim 1, wherein the expandable spacer comprises a first height between the first and second endplates in the first configuration and second height between the first and second endplates in the second configuration; and
    wherein the second height in greater than the first height.

9. The expandable spacer of claim 1, wherein the main body comprises at least one support member on the main body top surface and the main body bottom surface such that each support member is directly opposite to each other.

10. The expandable spacer of claim 1, wherein the expandable spacer comprises a first angle between the first and second endplates in the first configuration and second angle between the first and second endplates in the second configuration; and
    wherein the second angle in greater than the first angle.

11. An expandable intervertebral spacer having a first configuration and a second configuration, comprising:
    a main body having a main body first lateral wall, a main body second lateral wall having a threaded opening, a main body inner surface, a main body outer surface, a main body third lateral wall connecting the main body first lateral wall to the main body second lateral wall and including at least one opening extending entirely through the main body third lateral wall, a main body fourth lateral wall connecting the main body first lateral wall to the main body second lateral wall and including at least one opening extending entirely through the main body fourth lateral wall, the main body first lateral wall, the main body second lateral wall, the main body third lateral wall, and the main body fourth lateral wall defining a main body interior chamber;

a first endplate having a first endplate first end, a first endplate second end, a first endplate inner surface, a first endplate outer surface, at least two first endplate slots extending between the first endplate inner surface and the first endplate outer surface, a first extension extending from the first endplate inner surface towards the main body and including at least two openings, a second extension extending from the first endplate inner surface towards the main body and including at least two openings;

a second endplate having a second endplate first end, a second endplate second end, a second endplate inner surface, a second endplate outer surface, at least one second endplate slot extending between the second endplate inner surface to the second endplate outer surface, a third extension extending from the second endplate inner surface towards the main body and including at least one opening, a fourth extension extending from the second endplate inner surface towards the main body and including at least two openings;

a driving member disposed within the main body interior cavity and comprising a driving member first lateral wall, a driving member second lateral wall, a driving member third lateral wall, and a driving member fourth lateral wall, the driving member second lateral wall having a channel that is disposed on a plane parallel to the driving member second lateral wall, the driving member third lateral wall disposes at one opening extending entirely through the driving member third lateral wall, the driving member fourth lateral wall disposes at least one opening extending entirely through the driving member fourth lateral wall;

an actuation member configured to be inserted into the threaded opening and defines a cam to interface with the channel of the driving member to transition the expandable spacer from the first configuration to the second configuration; and a plurality of pins, each pin having a first end and a second end,
wherein the first end or the second end of each pin is passed through and received by one opening disposed on the main body, one opening disposed on the first endplate, one opening disposed on the second endplate, and one opening disposed on the driving member to assemble the main body, the first endplate, the second endplate, and the driving member together.

12. The expandable spacer of claim 11, wherein the driving member comprises a driving member interior chamber that is free and unobstructed.

13. The expandable spacer of claim 11, wherein the first endplate outer surface defines a first set of protruding ridges configured to engage a first vertebral body.

14. The expandable spacer of claim 11, wherein the second endplate outer surface defines a second set of protruding ridges configured to engage a second vertebral body.

15. The expandable spacer of claim 11, wherein at least one extension of the second endplate is disposed inside at least one slot of the first endplate when the expandable is in the first configuration; and
wherein the extension of the second endplate is parallel to the first endplate outer surface.

16. The expandable spacer of claim 11, wherein the threaded opening is in fluid communication with the main body interior chamber.

17. The expandable spacer of claim 11, wherein at least one opening of the first endplate extension is measured at a first angle and at least one opening of the second endplate extension is measured at a second angle; and
wherein the first and second angles are congruent angles.

18. The expandable spacer of claim 11, wherein the expandable spacer comprises a first height between the first and second endplates in the first configuration and second height between the first and second endplates in the second configuration; and
wherein the second height in greater than the first height.

19. The expandable spacer of claim 11, wherein the expandable spacer comprises a first height between the first and second endplates in the first configuration and second height between the first and second endplates in the second configuration; and
wherein the second height in greater than the first height.

20. An expandable intervertebral spacer having a first configuration and a second configuration, comprising:
a main body having a main body first lateral wall, a main body second lateral wall having a threaded opening, a main body inner surface, a main body outer surface, a main body third lateral wall connecting the main body first lateral wall to the main body second lateral wall and including two openings equally spaced along the main body third lateral wall and extending entirely through the main body third lateral wall, a main body fourth lateral wall connecting the main body first lateral wall to the main body second lateral wall and including two openings equally spaced along the main body third lateral wall and extending entirely through the main body fourth lateral wall, the main body first lateral wall, the main body second lateral wall, the main body third lateral wall, and the main body fourth lateral wall defining a main body interior chamber;

a first endplate having a first endplate first end, a first endplate second end, a first endplate inner surface, a first endplate outer surface, first, second, and third oblong first endplate slots extending between the first endplate inner surface and the first endplate outer surface, a first extension extending from the first endplate inner surface towards the main body and including at least two oblong openings, a second extension extending from the first endplate inner surface towards the main body and including at least two oblong openings;

a second endplate having a second endplate first end, a second endplate second end, a second endplate inner surface, a second endplate outer surface, a first, second, and third oblong second endplate slot extending between the second endplate inner surface to the second endplate outer surface, a third extension extending from the second endplate inner surface towards the main body and including at least one opening, a fourth extension extending from the second endplate inner surface towards the main body and including at least two oblong openings;

a driving member disposed within the main body interior cavity and comprising a driving member first lateral wall, a driving member second lateral wall, a driving member third lateral wall, and a driving member fourth lateral wall, the driving member second lateral wall having a channel that is disposed on a plane parallel to the driving member second lateral wall, the driving member third lateral wall disposes two openings equally spaced along the driving member third lateral wall and extending entirely through the driving member third lateral wall, the driving member fourth lateral wall disposes two openings equally spaced along the main body third lateral wall and extending entirely through the driving member fourth lateral wall;

an actuation member configured to be inserted into the threaded opening and defines a cam to interface with the channel of the driving member to transition the expandable spacer from the first configuration to the second configuration; and a plurality of pins, each pin having a first end and a second end, wherein the first end or the second end of each pin is passed through and received by one opening disposed on the main body, one opening disposed on the first endplate, one opening disposed on the second endplate, and one opening disposed on the driving member to assemble the main body, the first endplate, the second endplate, and the driving member together.

* * * * *